US012594182B2

(12) United States Patent
Davis et al.

(10) Patent No.: US 12,594,182 B2
(45) Date of Patent: Apr. 7, 2026

(54) DEVICES AND METHODS FOR URINE COLLECTION

(71) Applicant: Sage Products LLC, Cary, IL (US)

(72) Inventors: Gregory T. Davis, Woodstock, IL (US); Brett C. Blabas, Naperville, IL (US); Ryan A. Alvarez, Chicago, IL (US); Kristin M. Sexton, Cary, IL (US); Adam R. Cole, Cary, IL (US); Timothy J. Rapinchuk, Cary, IL (US); Catherine S. Boulos, Vernon Hills, IL (US)

(73) Assignee: Sage Products, LLC, Cary, IL (US)

( * ) Notice: Subject to any disclaimer, the term of this patent is extended or adjusted under 35 U.S.C. 154(b) by 0 days.

(21) Appl. No.: 18/735,612

(22) Filed: Jun. 6, 2024

(65) Prior Publication Data

US 2024/0315867 A1     Sep. 26, 2024

Related U.S. Application Data

(63) Continuation of application No. 18/197,922, filed on May 16, 2023, now Pat. No. 12,042,422, which is a
(Continued)

(51) Int. Cl.
*A61F 5/451*          (2006.01)
*A61B 5/20*          (2006.01)
(Continued)

(52) U.S. Cl.
CPC .............. *A61F 5/451* (2013.01); *A61B 5/208* (2013.01); *A61F 5/4408* (2013.01); *A61F 5/455* (2013.01); *A61M 2202/0496* (2013.01)

(58) Field of Classification Search
CPC .. A61F 5/451; A61F 5/455; A61F 5/44; A61F 5/4556
See application file for complete search history.

(56) References Cited

U.S. PATENT DOCUMENTS 3,349,768  A     10/1967  Keane
3,528,423  A      9/1970  Lee
(Continued)

FOREIGN PATENT DOCUMENTS

GB          2199750          7/1988
JP        2001-276107       10/2011
WO          01/54633         8/2001

OTHER PUBLICATIONS

English Translation of Abstract of Japanese Patent Application No. 2001-276107 dated Jun. 1, 2021.
(Continued)

*Primary Examiner* — Jessica Arble
*Assistant Examiner* — Meagan Ngo
(74) *Attorney, Agent, or Firm* — McDonnell Boehnen Hulbert & Berghoff LLP

(57)          ABSTRACT

A device for collecting urine discharged from a body of a user includes a fluid collection assembly having at least one layer for drawing urine discharged from the body into an interior cavity, an external covering that covers a portion of the at least one layer, and at least one fenestration for receiving urine, wherein the fenestration is a portion of the fluid collection assembly that is uncovered by the external covering. The device further includes a cap enclosing a first end of the assembly, a tube having a first end in fluid communication with the cap, and a shape retaining element configured to conform the assembly to a curved configuration and maintain the curved configuration until the configuration is adjusted. The assembly is configured to be disposed against the body of the user, with the at least one fenestration in operative relation with a urethral opening of the user.

23 Claims, 42 Drawing Sheets

Related U.S. Application Data continuation of application No. 17/873,097, filed on Jul. 25, 2022, now Pat. No. 11,839,567, which is a continuation of application No. 16/950,444, filed on Nov. 17, 2020, now Pat. No. 11,426,303, which is a continuation of application No. 15/896,325, filed on Feb. 14, 2018, now Pat. No. 10,857,025.

(60) Provisional application No. 62/458,917, filed on Feb. 14, 2017, provisional application No. 62/514,566, filed on Jun. 2, 2017, provisional application No. 62/556,318, filed on Sep. 8, 2017.

(51) Int. Cl.
    *A61F 5/44*        (2006.01)
    *A61F 5/455*       (2006.01)

(56)                References Cited

U.S. PATENT DOCUMENTS

| | | | |
|---|---|---|---|
| 3,613,123 | A | 10/1971 | Langstrom |
| 3,661,155 | A | 5/1972 | Lindan |
| 3,722,503 | A | 3/1973 | Hovick |
| 4,681,572 | A | 7/1987 | Tokarz et al. |
| 4,747,166 | A | 5/1988 | Kuntz |
| 4,804,377 | A | 2/1989 | Hanifl et al. |
| 4,820,297 | A | 4/1989 | Kaufman |
| 4,846,818 | A | 7/1989 | Keldahl |
| 4,886,508 | A | 12/1989 | Washington |
| 5,049,144 | A | 9/1991 | Payton |
| 5,678,564 | A | 10/1997 | Thompson |
| 6,551,292 | B1 | 4/2003 | D'Acchioli |
| 6,569,133 | B2 | 5/2003 | Cheng |
| 6,592,560 | B2 | 7/2003 | Snyder |
| 7,135,012 | B2 | 11/2006 | Harvie |
| 7,186,245 | B1 | 3/2007 | Cheng |
| 7,220,250 | B2 | 5/2007 | Suzuki |
| 7,390,320 | B2 | 6/2008 | Machida |
| 7,695,459 | B2 | 4/2010 | Gilbert |
| 7,695,460 | B2 | 4/2010 | Wada |
| 7,699,818 | B2 | 4/2010 | Gilbert |
| 7,727,206 | B2 | 6/2010 | Gorres |
| 7,740,620 | B2 | 6/2010 | Gilbert |
| 7,749,205 | B2 | 7/2010 | Tazoe |
| 7,755,497 | B2 | 7/2010 | Wada |
| 7,833,169 | B2 | 11/2010 | Hannon |
| 7,939,706 | B2 | 5/2011 | Okabe |
| 8,287,508 | B1 * | 10/2012 | Sanchez ................ A61F 5/4404 |
| | | | 604/326 |
| 8,303,554 | B2 | 11/2012 | Tsai |
| 8,343,122 | B2 | 1/2013 | Gorrez |
| 8,388,588 | B2 | 3/2013 | Wada |
| 9,173,602 | B2 | 11/2015 | Gilbert |
| 9,173,799 | B2 | 11/2015 | Tanimoto |
| 10,226,376 | B2 | 3/2019 | Sanchez |
| 10,376,406 | B2 | 8/2019 | Newton |
| 10,376,407 | B2 | 8/2019 | Newton |
| 10,390,989 | B2 | 8/2019 | Sanchez |
| D882,768 | S | 4/2020 | Davis |
| 10,857,025 | B2 | 12/2020 | Davis et al. |
| 10,973,678 | B2 | 4/2021 | Newton |
| 11,376,152 | B2 | 7/2022 | Sanchez |
| 11,382,786 | B2 | 7/2022 | Sanchez |
| 11,426,303 | B2 | 8/2022 | Davis |
| 11,865,030 | B2 | 1/2024 | Davis |
| 11,890,221 | B2 | 2/2024 | Ulreich |
| 11,938,053 | B2 | 3/2024 | Austermann |
| 2001/0037098 | A1 | 11/2001 | Snyder |
| 2003/0046753 | A1 | 3/2003 | Buttigieg |
| 2004/0176731 | A1 | 9/2004 | Cheng |
| 2004/0191919 | A1 | 9/2004 | Unger |
| 2004/0254547 | A1 | 12/2004 | Okabe |
| 2005/0070861 | A1 | 3/2005 | Okabe |
| 2005/0119630 | A1 | 6/2005 | Harvie |
| 2006/0163097 | A1 | 7/2006 | Murray et al. |
| 2007/0038194 | A1 | 2/2007 | Wada et al. |
| 2007/0093840 | A1 | 4/2007 | Pacelli |
| 2008/0287894 | A1 | 11/2008 | Van Den Heuvel |
| 2010/0241104 | A1 | 9/2010 | Gilbert |
| 2010/0286791 | A1 | 11/2010 | Goldsmith |
| 2011/0028922 | A1 | 2/2011 | Kay |
| 2011/0077495 | A1 | 3/2011 | Gilbert |
| 2011/0172625 | A1 | 7/2011 | Wada |
| 2012/0103347 | A1 * | 5/2012 | Wheaton ................. A61F 5/453 |
| | | | 128/885 |
| 2012/0116336 | A1 | 5/2012 | Sharma |
| 2014/0157499 | A1 | 6/2014 | Suzuki |
| 2016/0029998 | A1 | 2/2016 | Brister |
| 2016/0058322 | A1 | 3/2016 | Brister |
| 2016/0278662 | A1 | 9/2016 | Brister |
| 2016/0367226 | A1 | 12/2016 | Newton |
| 2016/0374848 | A1 * | 12/2016 | Sanchez ................. A61F 5/455 |
| | | | 604/319 |
| 2017/0246026 | A1 * | 8/2017 | Laniado ................ A61F 5/4408 |
| 2017/0266031 | A1 | 9/2017 | Sanchez et al. |
| 2018/0228642 | A1 | 8/2018 | Davis |
| 2019/0282391 | A1 | 9/2019 | Johannes |
| 2019/0336319 | A1 | 11/2019 | Fallis |
| 2019/0365561 | A1 | 12/2019 | Newton |
| 2021/0059853 | A1 | 3/2021 | Davis et al. |
| 2021/0069008 | A1 | 3/2021 | Blabas et al. |
| 2022/0354685 | A1 | 11/2022 | Davis et al. |

OTHER PUBLICATIONS

International Search Report and Written Opinion for International Application No. PCT/US2018/018112, dated Jun. 6, 2018 (10 pages).

* cited by examiner

10

30     40

50

28

24

22

20

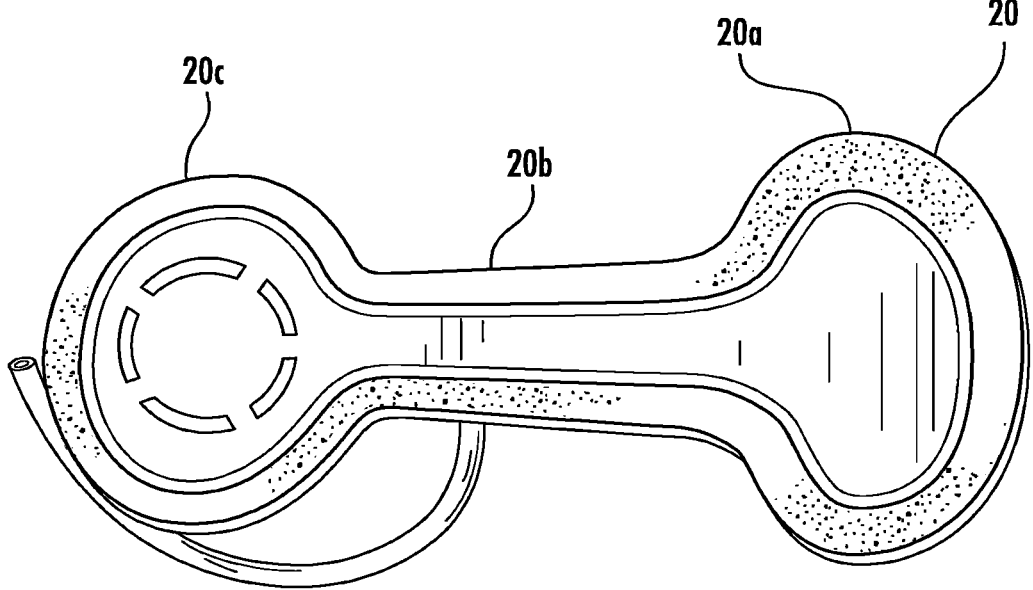
FIG. *8*

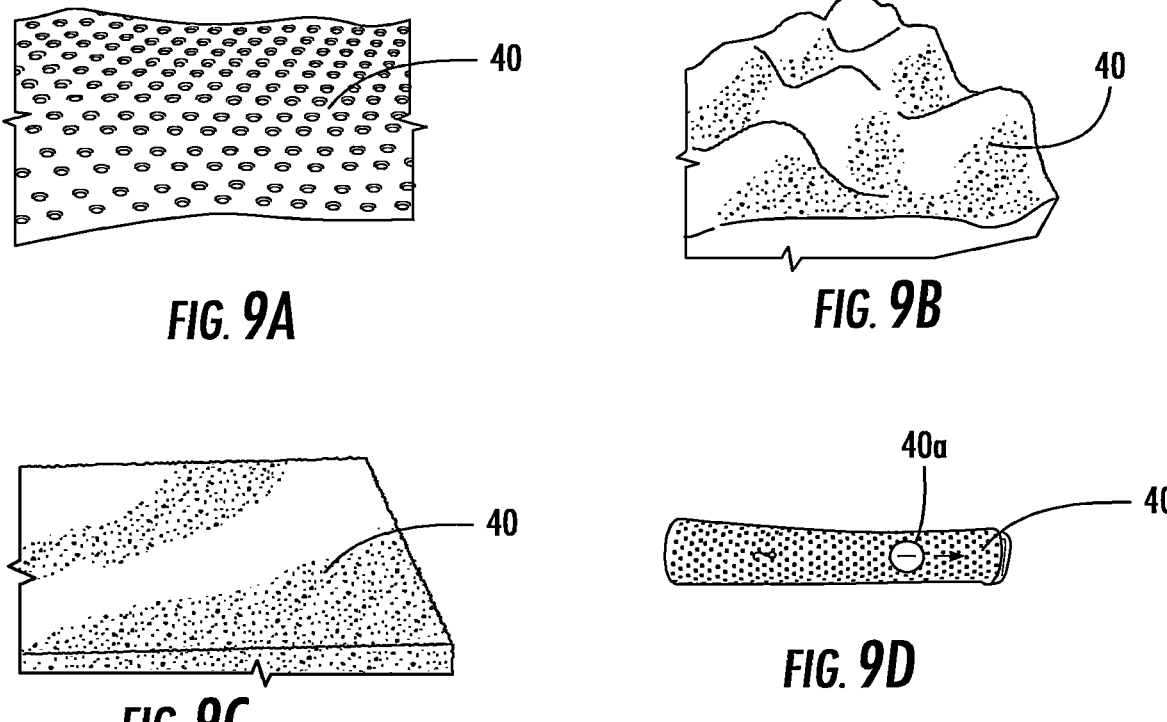
*FIG. 9A*
*FIG. 9B*
*FIG. 9C*
*FIG. 9D*
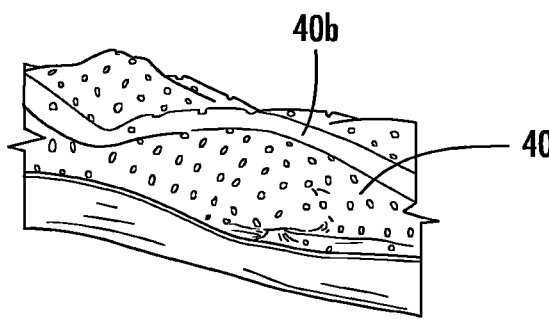
*FIG. 9E*

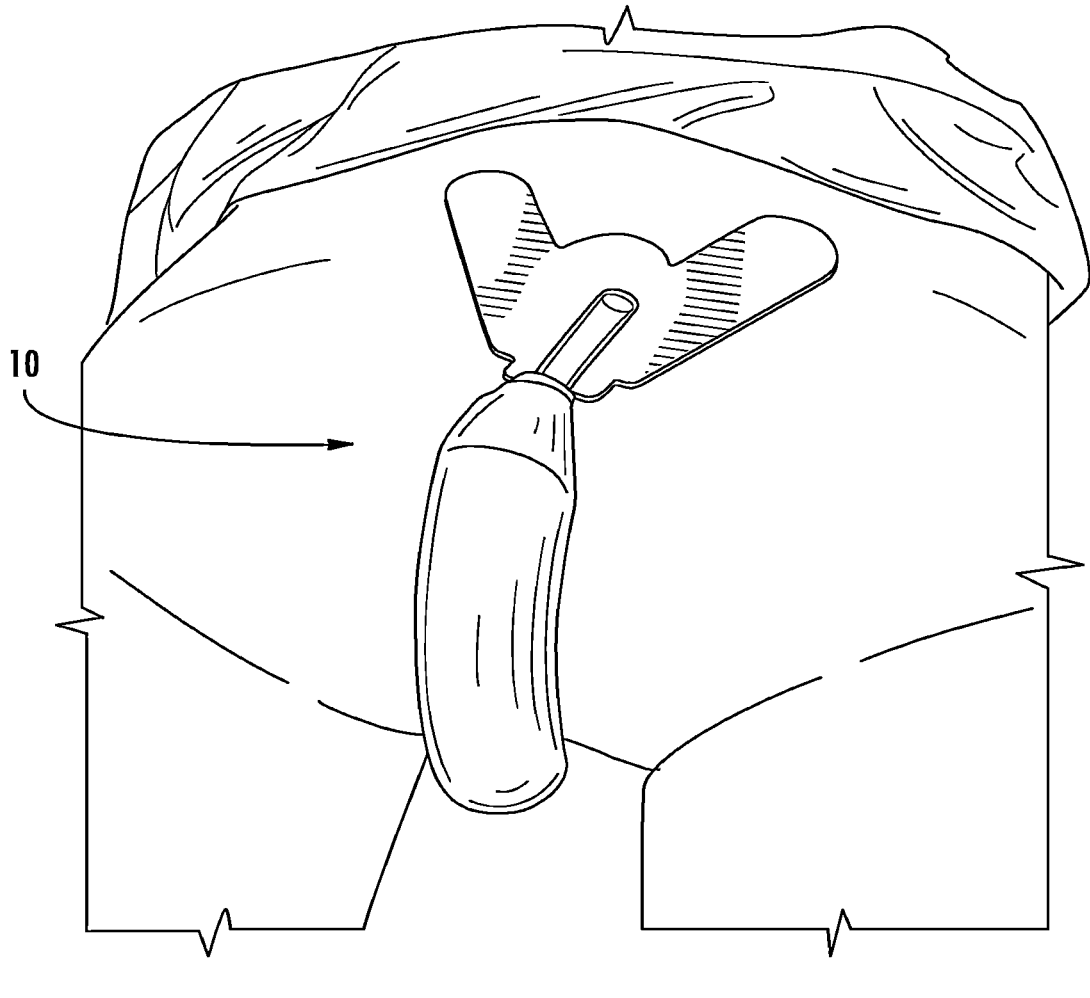
10
FIG. *10*

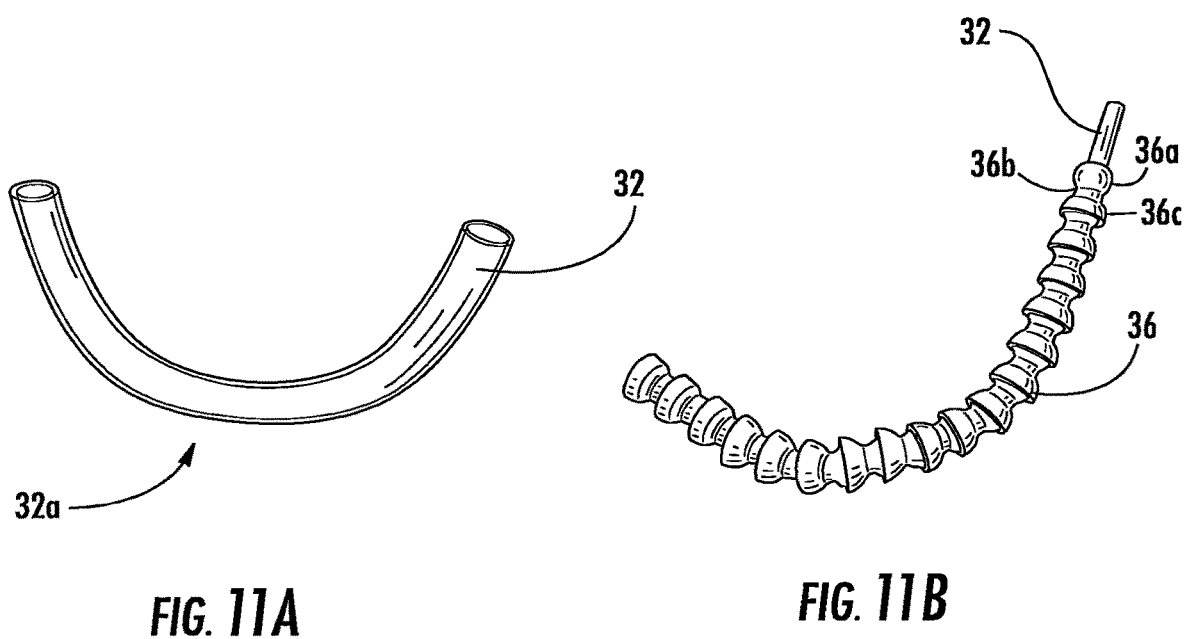
FIG. *11A*
FIG. *11B*
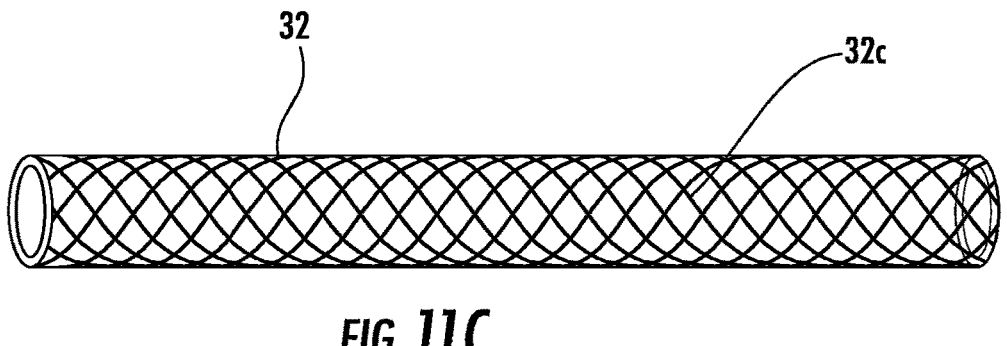
FIG. *11C*

32d
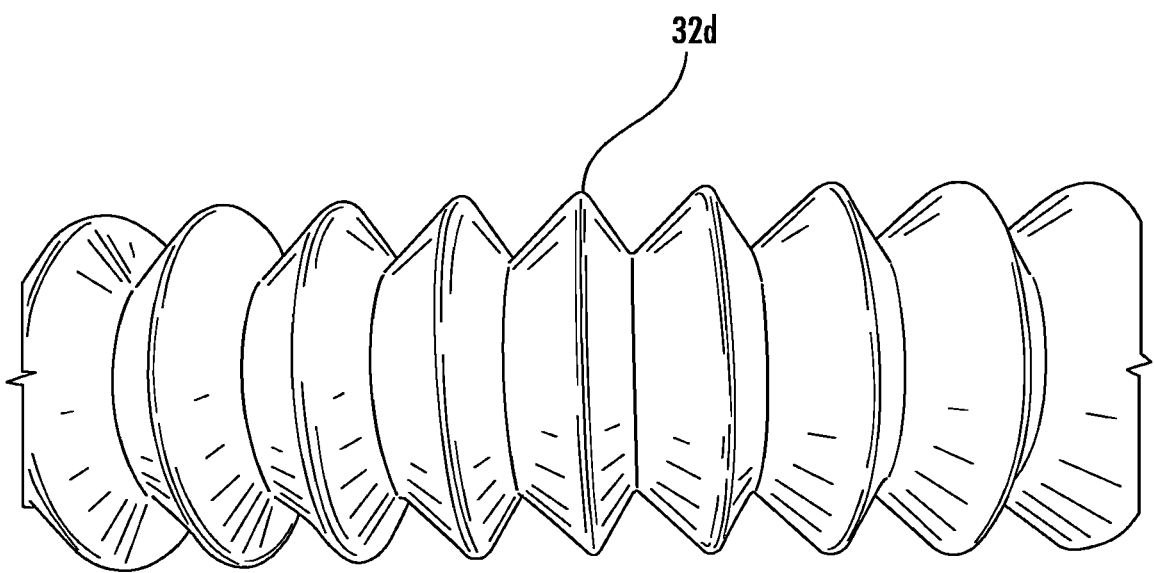
*FIG.* 11D

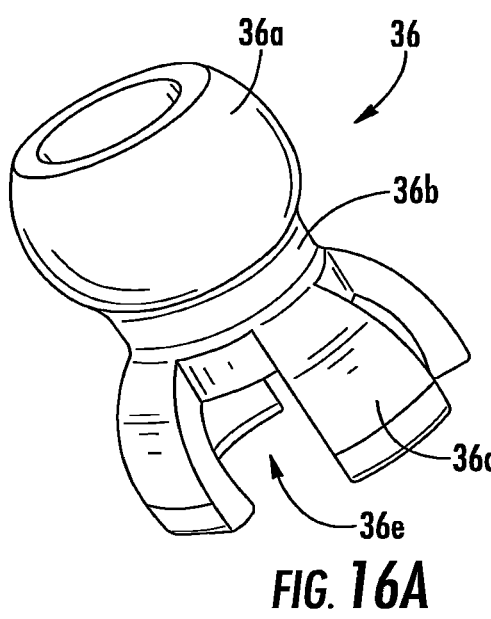
*FIG.* 16A
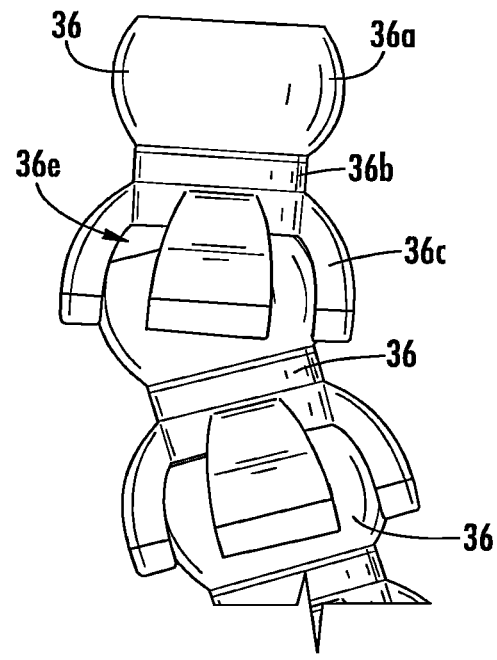
*FIG.* 16B
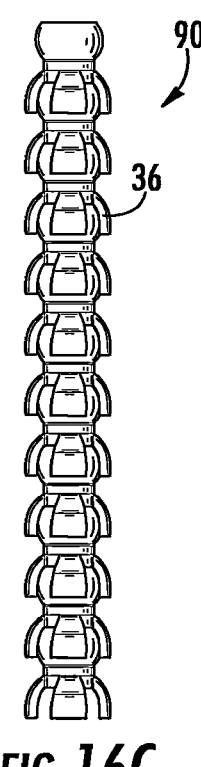
*FIG.* 16C

28

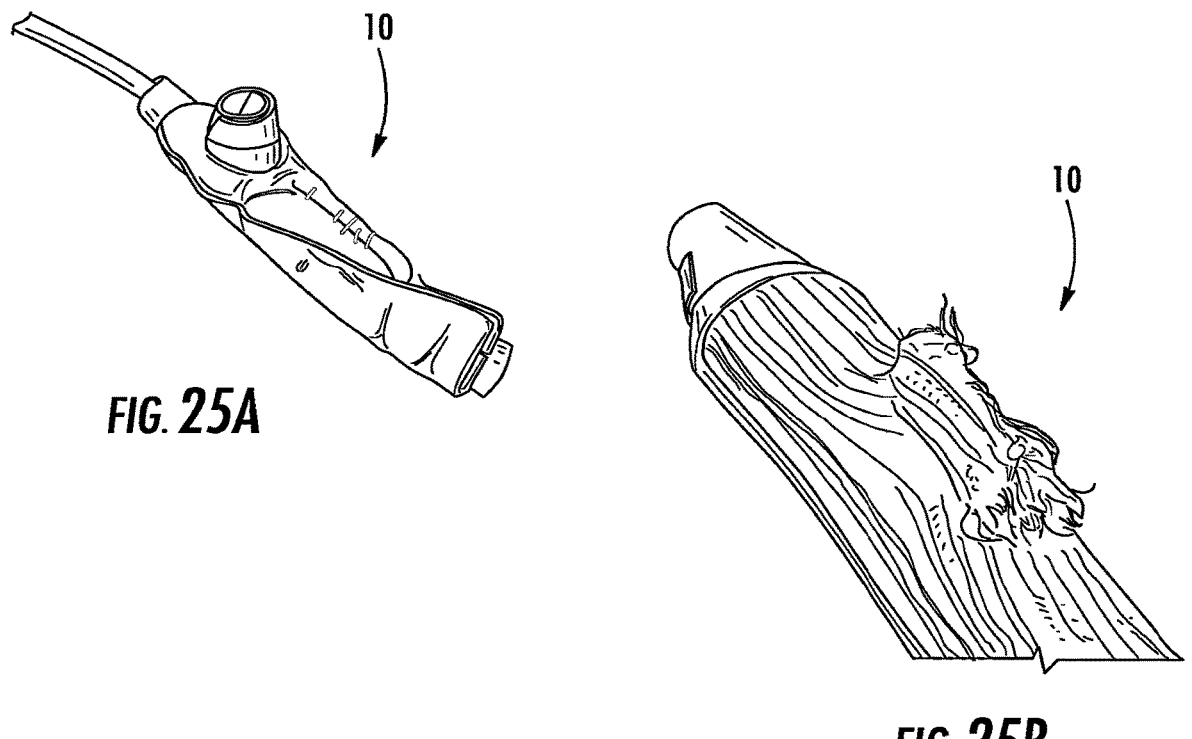
FIG. 25A
FIG. 25B
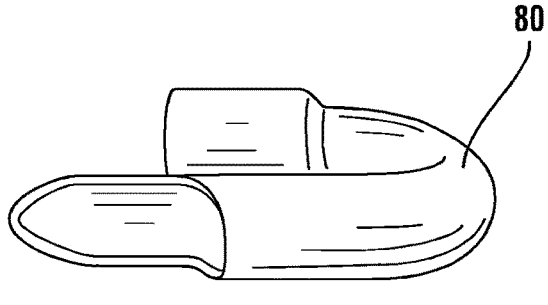
FIG. 25C

70
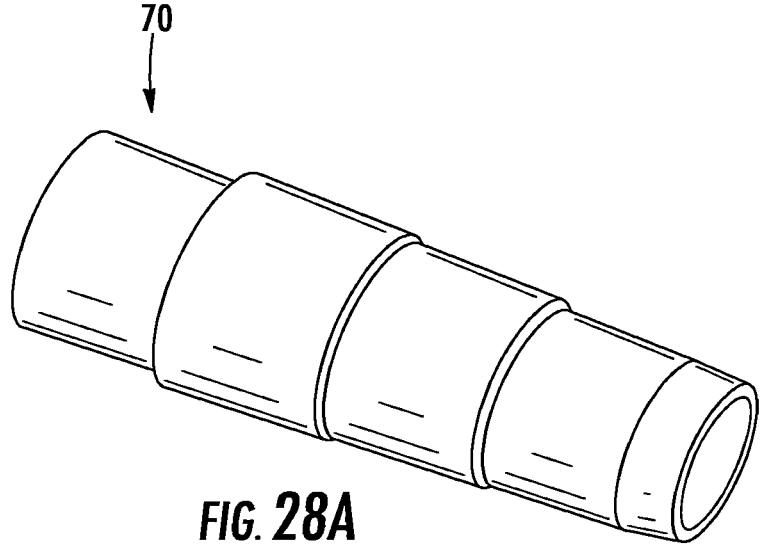
*FIG.* 28A
70
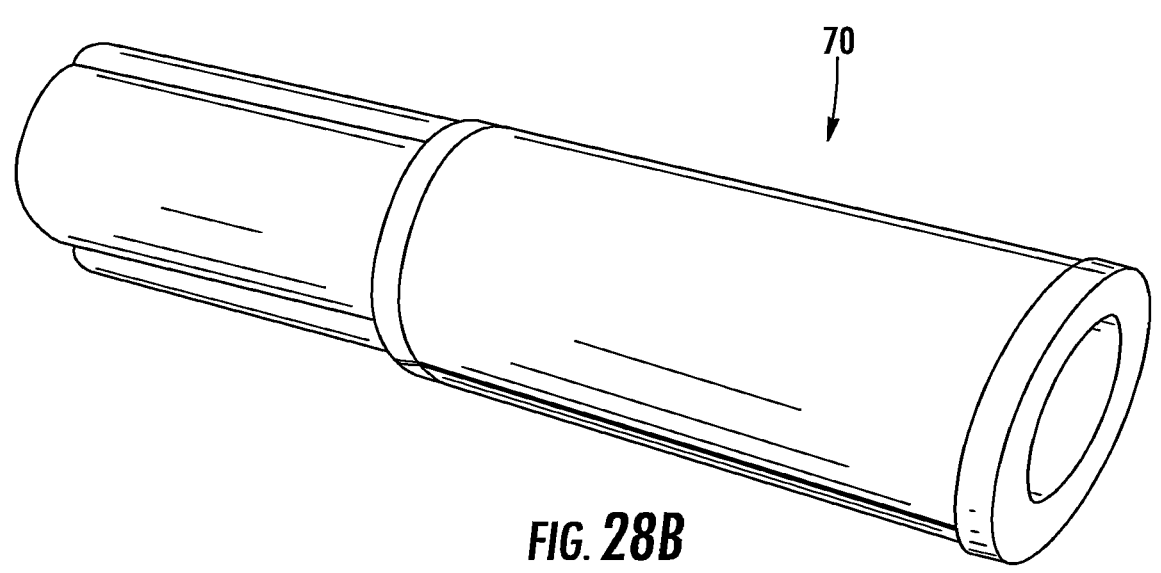
*FIG.* 28B

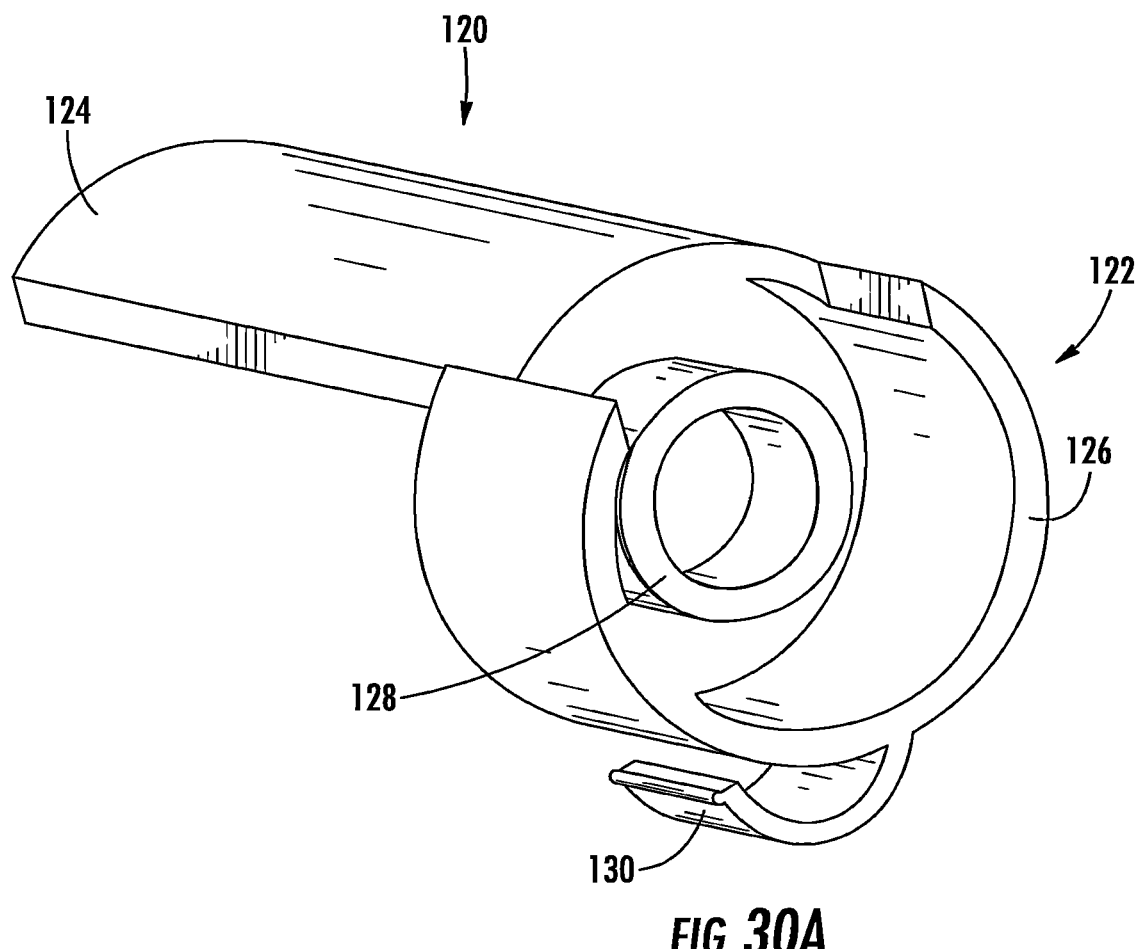
*FIG.* 30A

300

301
COUPLE VACCUUM LINE TO VACCUUM SOURCE

302
COUPLE DISCHARGE LINE TO FLUID RECEPTACLE

303
POSITION URINE COLLECTION DEVICE
IN CONTACT WITH THE PATIENT

304
COUPLE DISCHARGE LINE TO DEVICE TUBE

305
ACTIVATE SUCTION AND COLLECT URINE VOIDED
FROM THE PATIENT

306
REMOVE DEVICE FROM PATIENT AND REPLACE
AS NEEDED

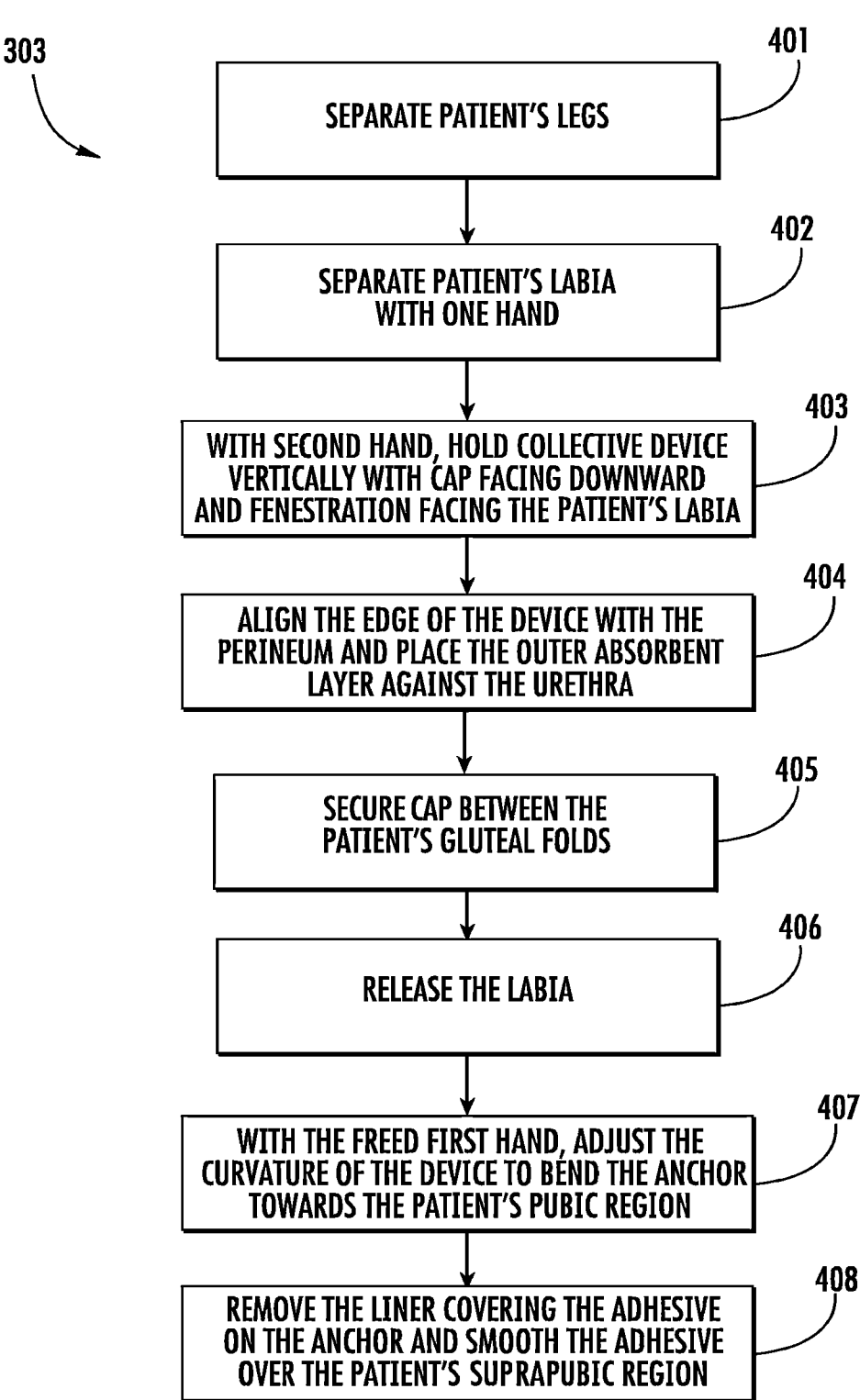

303

401
SEPARATE PATIENT'S LEGS

402
SEPARATE PATIENT'S LABIA
WITH ONE HAND

403
WITH SECOND HAND, HOLD COLLECTIVE DEVICE
VERTICALLY WITH CAP FACING DOWNWARD
AND FENESTRATION FACING THE PATIENT'S LABIA

404
ALIGN THE EDGE OF THE DEVICE WITH THE
PERINEUM AND PLACE THE OUTER ABSORBENT
LAYER AGAINST THE URETHRA

405
SECURE CAP BETWEEN THE
PATIENT'S GLUTEAL FOLDS

406
RELEASE THE LABIA

407
WITH THE FREED FIRST HAND, ADJUST THE
CURVATURE OF THE DEVICE TO BEND THE ANCHOR
TOWARDS THE PATIENT'S PUBIC REGION

408
REMOVE THE LINER COVERING THE ADHESIVE
ON THE ANCHOR AND SMOOTH THE ADHESIVE
OVER THE PATIENT'S SUPRAPUBIC REGION

FIG. 34

DEVICES AND METHODS FOR URINE COLLECTION

CROSS-REFERENCE TO RELATED PATENT APPLICATIONS

This application is a continuation of U.S. Non-Provisional application Ser. No. 18/197,922, filed May 16, 2023, which is a continuation of U.S. Non-Provisional application Ser. No. 17/873,097, filed Jul. 25, 2022, which is a continuation of U.S. Non-Provisional application Ser. No. 16/950,444 entitled "Devices and Methods for Urine Collection, filed Nov. 17, 2020, which is a continuation of U.S. Non-Provisional application Ser. No. 15/896,325 entitled "Devices and Methods for Urine Collection", filed on Feb. 14, 2018, which claims priority to (i) U.S. Provisional Patent Application No. 62/458,917, filed Feb. 14, 2017, (ii) U.S. Provisional Patent Application No. 62/514,566, filed Jun. 2, 2017, and (iii) U.S. Provisional Patent Application No. 62/556,318, filed on Sep. 8, 2017, the contents of each of which are hereby incorporated by reference in their entirety.

BACKGROUND

The present disclosure generally relates to devices, systems, and methods for collecting urine discharged from the body of a user and carrying the urine away from the body.

Under various circumstances, a user may have limited or impaired mobility such that ordinary urinary functions and processes are rendered difficult or even impossible. For example, a person may have impaired mobility due to a disability or may be bedridden due to injury or illness. In another example, a person may be subject to restricted occupational conditions under which the person has limited mobility. Finally, urine collection may be needed for monitoring purposes, such as for monitoring inputs and outputs in a clinical setting (e.g. in the ICU, or for other clinical and/or laboratory testing).

Various approaches have been developed to address some of the problems or circumstances related to impaired or restricted urinary processes. However, the prior approaches suffer from problems or limitations of their own. Urinary catheters, for example, can address problems arising from urinary incontinence or limited mobility, but urinary catheters can often be uncomfortable and can contribute to complications (for example, infections). Bed pans, as another example, are containers occasionally used for collecting urinary output of a bedridden person (such as a patient at a health care facility), but bed pans can contribute to patient discomfort, spillage, and issues related to sanitation or hygiene.

BRIEF DESCRIPTION OF THE DRAWINGS

FIG. 8 depicts an alternative exemplary embodiment of an external covering of a urine collection FIGS. 9A-E depict various exemplary materials and embodiments of an outer collection layer of a urine collection device.

FIG. 10 depicts the placement of the device illustrated in FIG. 1 on the body of a female patient.

FIGS. 11A-D depict various exemplary embodiments of a tube of a urine collection device.

FIG. 16A is a side perspective view of a linking segment of a shape retaining element, according to an exemplary embodiment.

FIG. 16B is a side view of multiple linking segments illustrated in FIG. 16A, according to an exemplary embodiment.

FIG. 16C is a side view of a shape retaining element formed from multiple linking segments illustrated in FIG. 16A, according to an exemplary embodiment.

FIGS. 25A-C depict various alternative exemplary embodiments of a urine collection device.

FIG. 28A-B depict side perspective views of a tube adaptor, according to exemplary embodiments.

FIGS. 30A-B depict various perspective views of another cap for use with a urine collection device, according to an exemplary embodiment.

FIG. 34 is a flow chart depicting a method of positioning a urine collection device on a patient, according to an exemplary embodiment.

DETAILED DESCRIPTION

Figure 1:
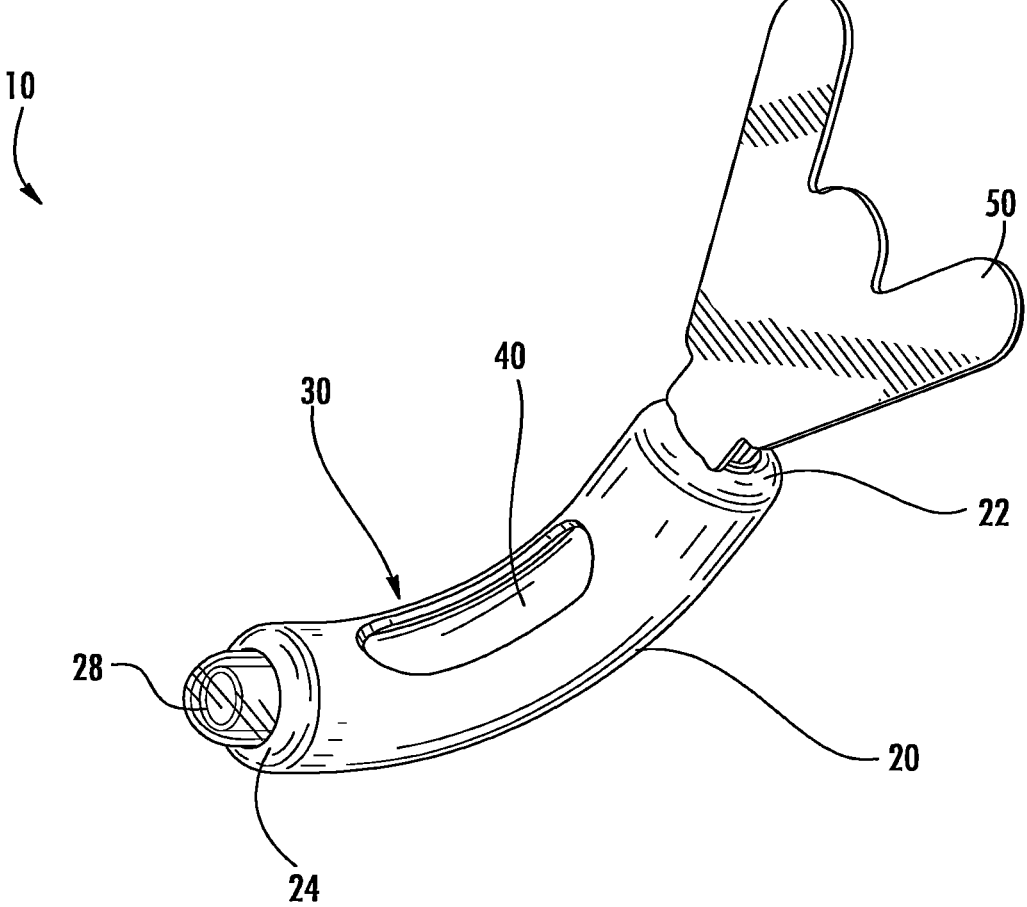
FIG. 1 is a top perspective view of a urine collection device according to an exemplary embodiment.
Figure 2:
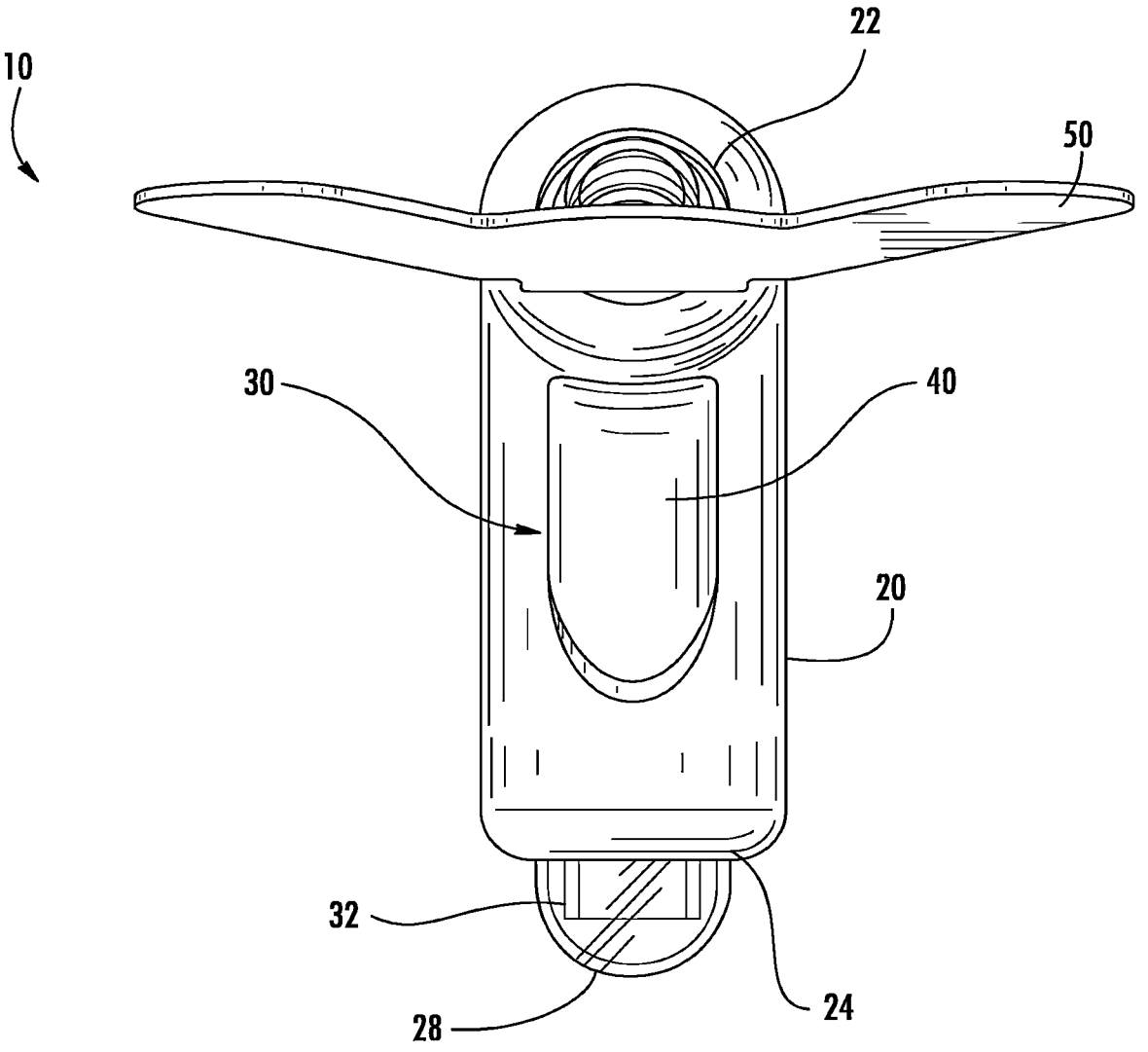
FIG. 2 is a top view of the device illustrated in FIG. 1.
Figure 3:
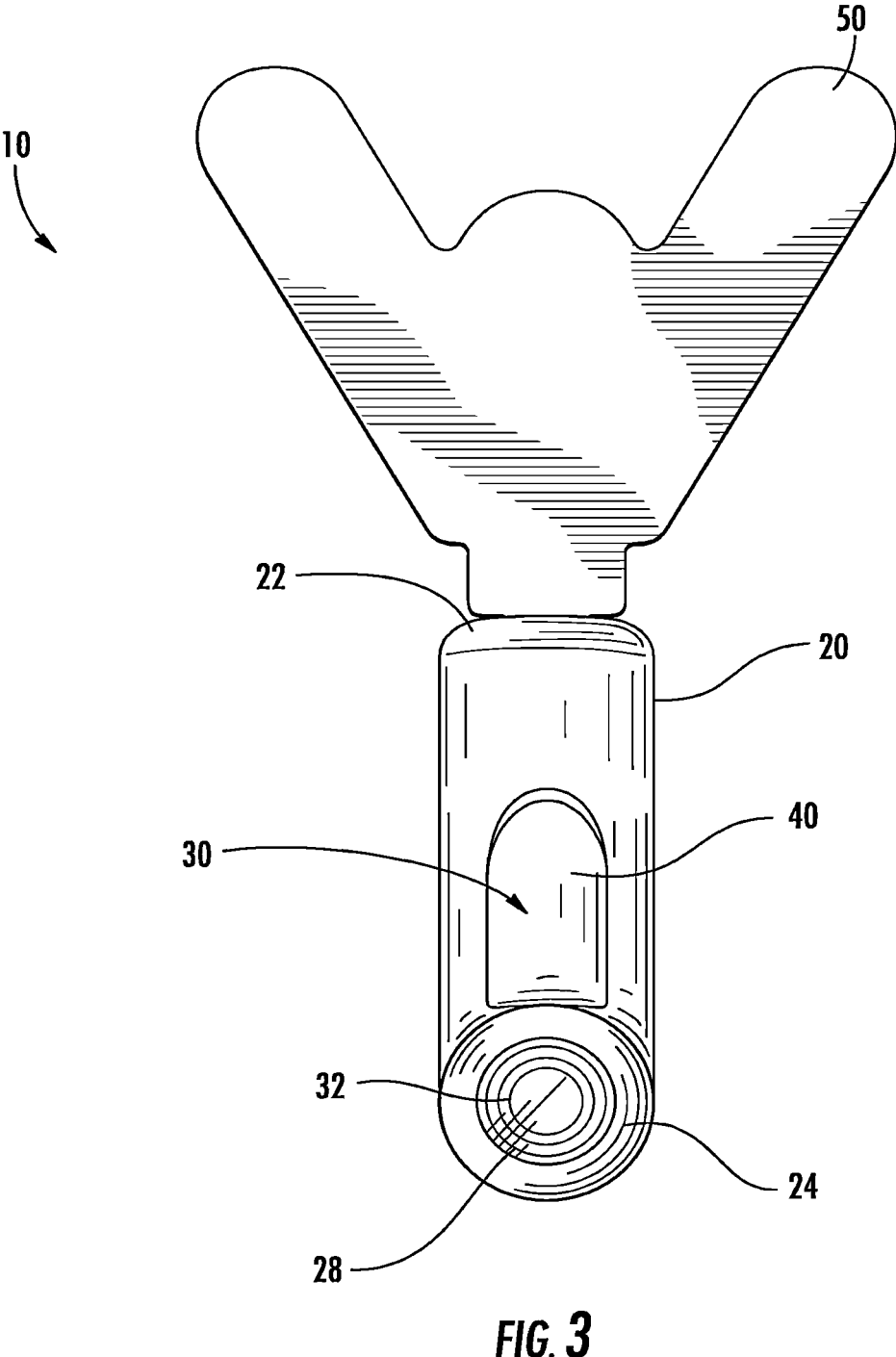
FIG. 3 is a front view of the device illustrated in FIG. 1.
Figure 4:
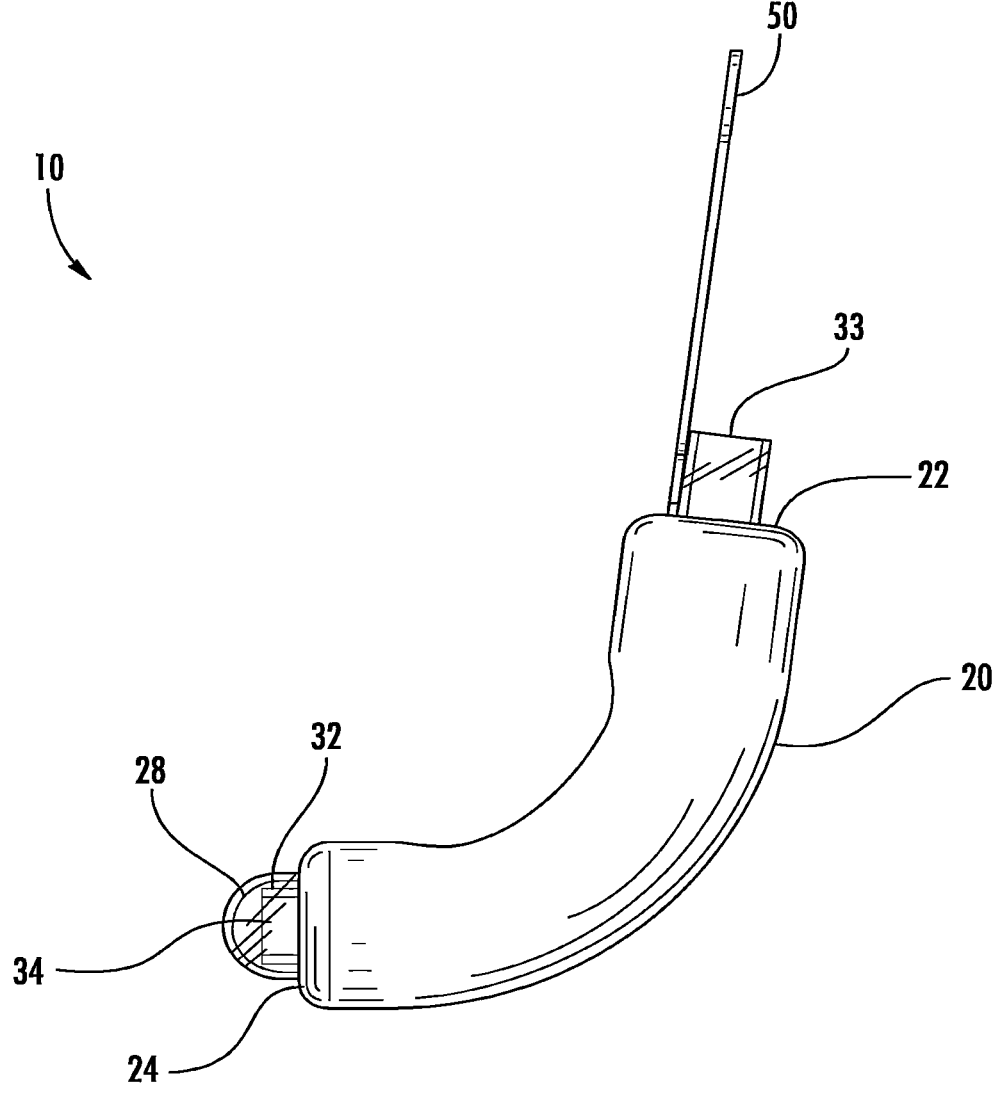
FIG. 4 is a side view of the device illustrated in FIG. 1.
Figure 5:
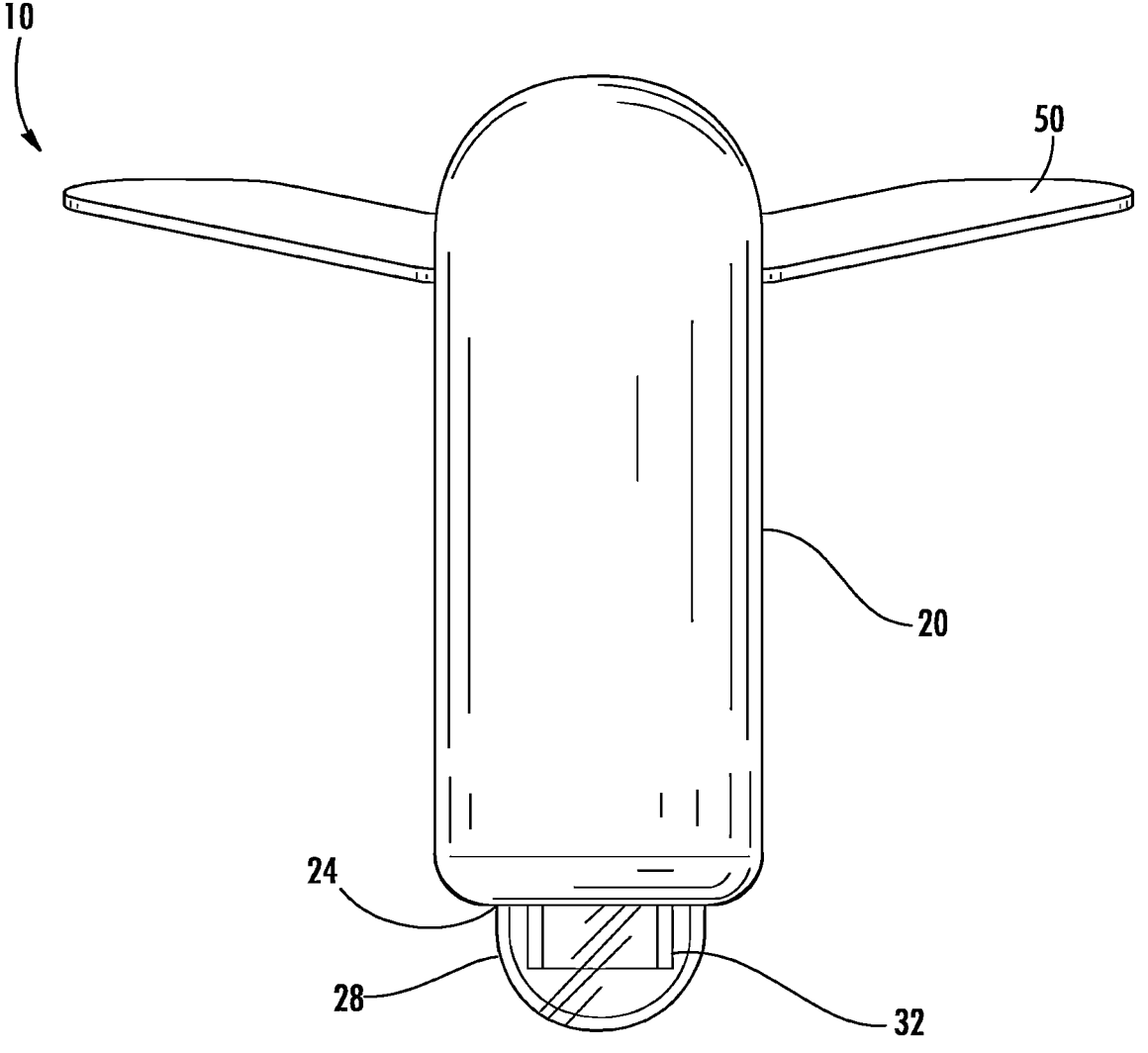
FIG. 5 is a bottom view of the device illustrated in FIG. 1.
Figure 6:
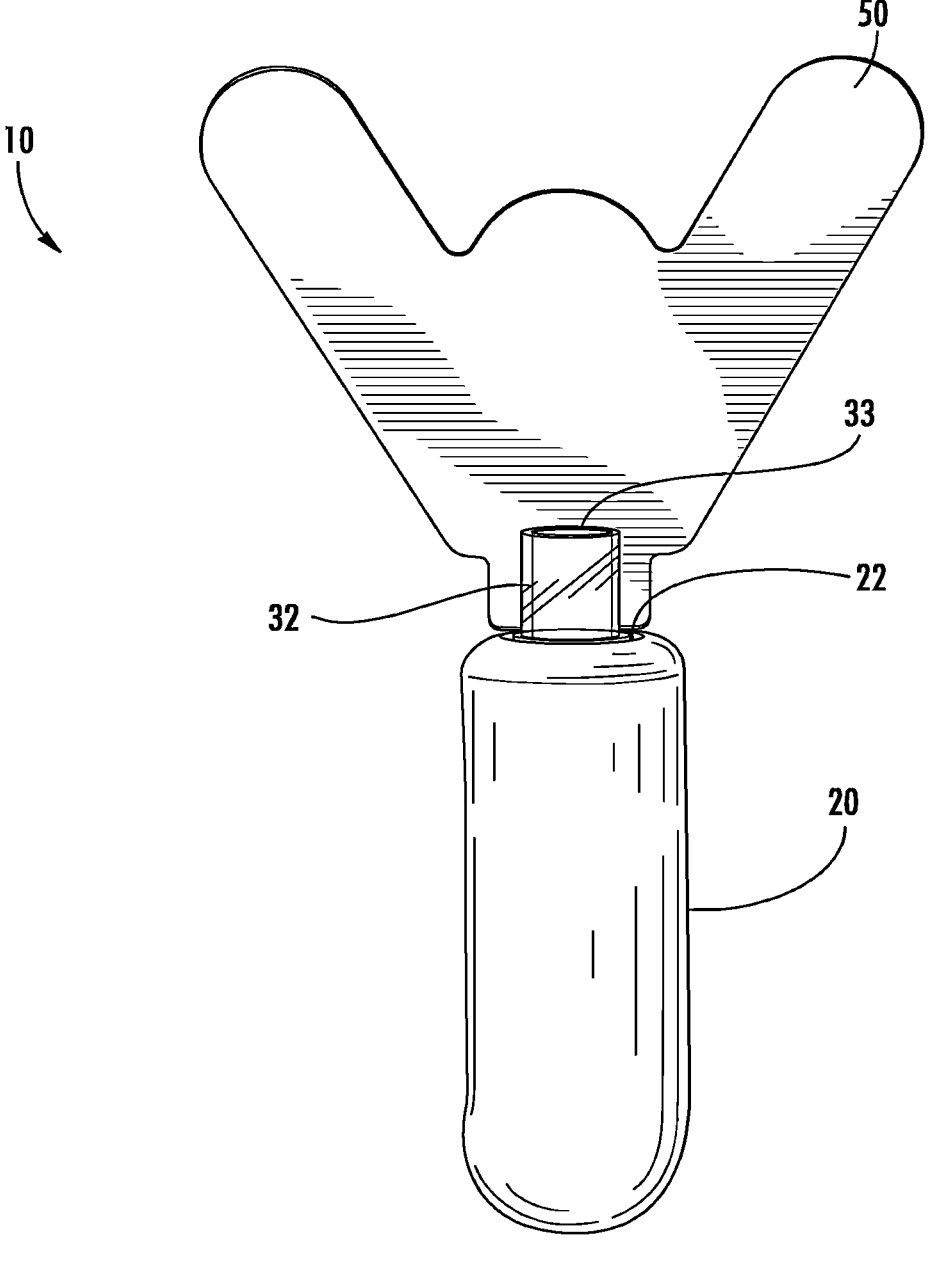
FIG. 6 is a rear view of the device illustrated in FIG. 1.

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

The figures generally show a device for collecting and removing urine that has been discharged from the body of a user, in particular a female user (e.g., a human female), according to various exemplary embodiments. However, it should be understood that the device described herein may be used with a variety of patients, including male patients with certain anatomical conditions. The device for collecting and removing urine discharged from a user is configured to hold its placement near the pelvic region on a body of a user such that fluid leakage from the device is minimized or eliminated.

Referring to FIGS. 1-7, a urine collection device 10 according to an exemplary embodiment of the present disclosure is shown. Urine collection device 10 includes an external covering 20 having an open first end 22 and an open second end 24. In an exemplary embodiment, the external covering 20 is fluid impermeable. A longitudinally extending fenestration 30 is disposed in a portion of the external covering 20 between the open first end 22 and the open second end 24. In some alternative embodiments, there is more than one fenestration in the external covering 20. The fenestration 30 is sized and positioned in the external covering 20 to be placed in the area of the patient's urethral opening, such that the fenestration 30 allows for fluid flow from an urethral opening of a user's body into a cavity defined by the external covering 20 and eventually out to the collection reservoir. In some embodiments, the fenestration 30 extends along an entire longitudinal direction of the external covering 20, extending an entire distance from the open first end 22 to the open second end 24.

The external covering 20 contains and diverts urine that enters through the fenestration 30 into a cap 28. From the cap 28, the urine is drawn into a tube 32 for removing the urine from the device 10. The external covering 20 is configured to hold the interior components of the urine collection device 10 together. The external covering 20 can be formed from a soft, skin-safe, and hydrophobic material such as silicone, polyurethane, or some other polymeric material in the form of a foam, coating, or a medical grade tape. In some embodiments, an outer surface of the external covering 20 is treated with or includes in its material a texture that grips the skin, which may provide greater stability for the device 10 to maintain its position.

In the embodiment depicted in FIG. 1, the external covering 20 takes on a curved, hollowed-out, three-dimensional obround shape which completely envelops one or more fluid collection layers, except for portions that are exposed through the fenestration 30.

In other embodiments, the external covering 20 has an alternative shape, such as that depicted in FIG. 8. Referring to FIG. 8, the external covering 20 has a first portion 20a configured to fit over the pubic region of the body of a user, a second portion 20b configured to fit the contours of the perineum of the body of a user, and a third portion 20c configured to cover the coccyx of a user. In one embodiment, the external covering 20 has a hydrophobic, closed-cell foam surface having channels that include a hydrophilic material. In other embodiments, the external covering is manufactured of a soft, hydrophobic material (e.g., silicone, polyurethane or other polymeric material) forming a foam or medical-grade tape. In some embodiments, a width of the first portion 20a and a width of the third portion 20c are approximately equal and a width of the second portion 20b is less than the widths of the first and third portions 20a and 20c, respectively.

Figure 7:
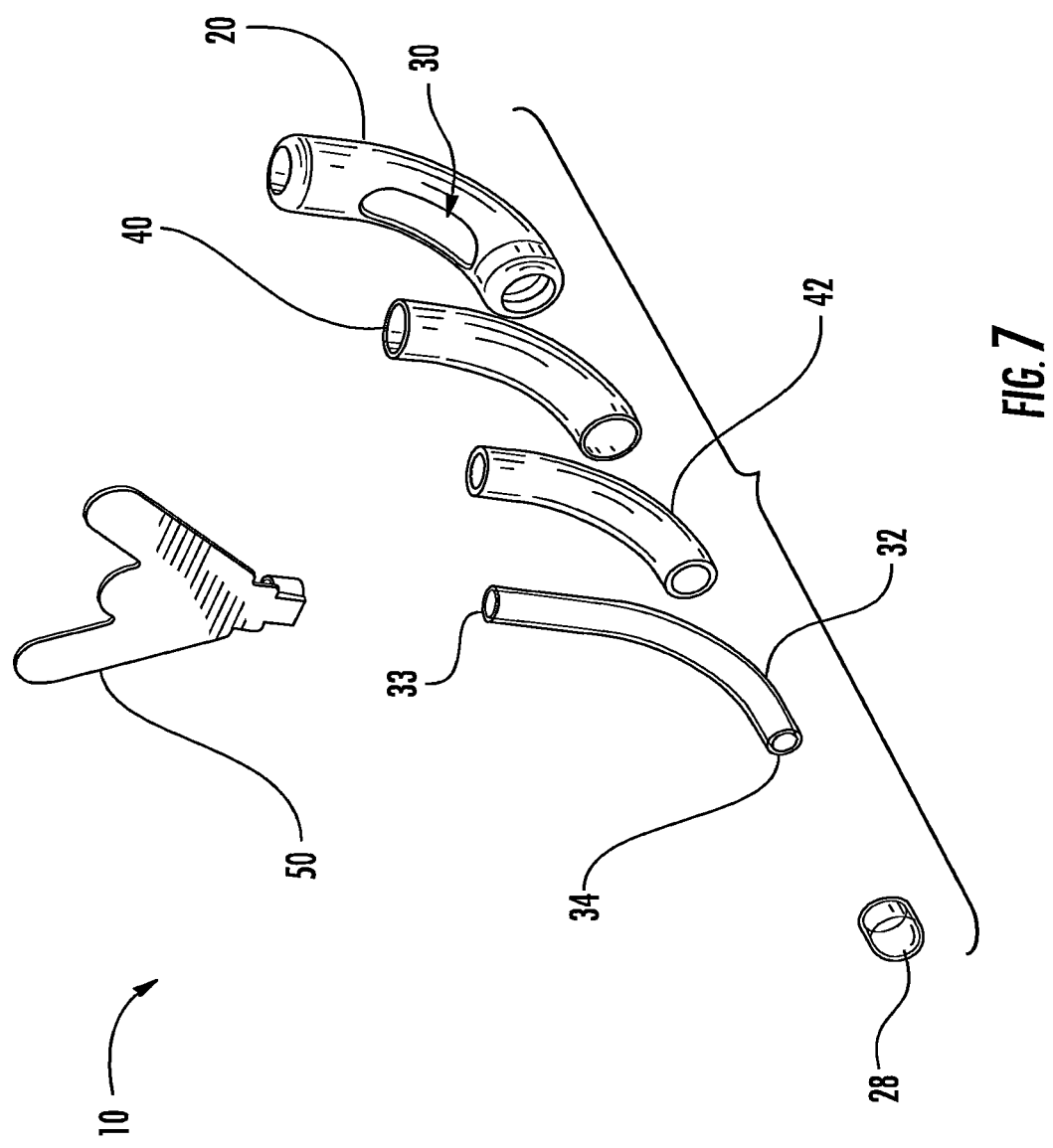
FIG. 7 is a perspective view of an exploded assembly of the device illustrated in FIG. 1.

Referring back to the urine collection device of FIGS. 1-7, and particularly to the exploded view of FIG. 7, the external covering 20 surrounds at least a portion of a fluid collection assembly, comprising one or more fluid collection layers that evacuate, draw through or absorb the voided urine. The fluid collection assembly is positioned within the external covering 20, with a portion of the fluid collection assembly exposed at the fenestration 30. In the embodiment shown, the fluid collection assembly includes an outer collection layer 40 and an inner collection core 42. In some embodiments, one or both of these layers are moisture wicking layers that evacuate the discharged fluid away from the body (e.g. by wicking or capillary effect). In this way, the layer(s) in direct contact with the anatomy do not feel wet to the user or cause dampness on the user's skin, improving user comfort. Furthermore, drawing urine away from the urethral opening of the user assists with preventing urine from leaking or flowing into the surrounding environment (e.g., a bed or chair). In other embodiments, one or more of the fluid collection layers absorb and hold fluid, in combination with or instead of wicking the fluid away.

In some embodiments, the outer collection layer 40 is formed of a material having a high absorptive and/or adsorption rate, and a high permeation rate such that urine can be rapidly wicked and diverted to the cavity of the device 10. FIGS. 9A-C depict examples of outer collection layers 40 that are fluid permeable (e.g., urine permeable) and have moisture-wicking properties. In one example, the outer collection layer 40 is manufactured of a piece of jersey mesh material, such as that used to make athletic clothing, as shown in FIG. 9A. The outer collection layer 40 may be made of polyester or a blend of polyester and spandex (e.g., a peephole mesh comprising 90% polyester and 10% spandex and weighing within 5% of 215 g). As a further example, shown in FIG. 9B, the outer collection layer 40 has a corrugated surface such that a surface of the outer collection layer 40 has open-cell foam ridges and grooves. This corrugated surface is configured to slow fluid flow at the surface and to provide an increased surface area for promoting fluid absorption and/or adsorption. As a further example, shown in FIG. 9C, the outer collection layer 40 has a moisture wicking foam surface manufactured from, for example, a polyurethane foam having open cells (e.g., a polyurethane foam having a density of 1.8 lb/ft³ and a pressure to compress 25% of 0.6 psi). In some configurations, the corrugated layer or foam layer further provides a cushion for surrounding the tube 32 in the device 10, to limit discomfort to the user caused by the rigidity of the tube 32.

Referring to FIG. 9D, in some embodiments, the outer collection layer 40 has one or more indicators 40a configured to assist a person (e.g., a healthcare worker) with optimal positioning of the device in relationship to the urethral opening of a patient. In some embodiments, the outer collection layer 40 has one or more raised ridges or grooves running therethrough, such as ridge 40b shown in FIG. 9E, creating raised grooves and ridges configured to slow the flow of fluid at the surface of the outer collection layer 40, which increases its ability to wick fluid and allow more efficient fluid flow through the outer collection layer 40 to the inner collection core 42. Grooves could also be sized and configured to wick urine away using capillary action.

Referring back to FIG. 7, an inner collection core 42 is positioned within the external covering 20 and inside of the outer collection layer 40. In some embodiments, the inner collection core 42 is positioned relative to the outer collection layer 40 so as to support and maintain the position of the outer collection layer 40 across the fenestration 30. The inner collection core 42 is formed of any suitable material and has suitable shape that allows for collecting fluid and/or directing fluid flow into an inner cavity of the device 10. The inner collection core 42, in this embodiment, is further configured to reduce the contact pressure of the tube 32 on the body of a user. For example, in some embodiments, the inner collection core 42 is a flexible material. In some embodiments, the inner collection core 42 is manufactured of a polyester filter material (e.g., Nu-Foam formed of a polyester staple fiber of polyethylene terephthalate) that draws the fluid from the outer collection layer 40 and wicks it into the cavity without retaining the fluid.

According to an exemplary embodiment, the tube 32 is manufactured of a semi-rigid material and extends within the external covering 20 between the open first end 22 and the open second end 24. Tube 32 allows a vacuum (e.g. a pressure lower than ambient air pressure) to be produced in the cavity of external covering 20 when suction is applied to the tube 32, such that fluid collected within the device 10 is evacuated from device 10 through tube 32. Tube 32 has a first end 33 configured to extend out from the first open end of the external covering 20 and a second end 34 terminating within the cap 28 (described below). Tube 32 is configured to evacuate fluid out from cap 28.

FIG. 10 depicts an exemplary positioning and use of the urine collection device 10 for a female patient. As shown in FIG. 10, the collection device 10 forms to the curvature of the female anatomy, and the lower end of the collection device 10 is configured to be secured or tucked between the gluteal folds and the perineum. In this way, the collection device 10 is in a position such that when the patient voids, the fluid is absorbed by or drawn through one or more fluid collection layers of the collection device 10 (described below), collected into a body of the collection device 10 and then diverted to a reservoir away from the body.

The urine collection device 10, according to an exemplary embodiment, includes a shape retaining element. The shape retaining element is a bendable element that is configured to conform the fluid collection assembly to a curved configuration for placement against the body of the user and maintain the curved configuration of the fluid collection assembly until the configuration is adjusted. In some embodiments, as depicted in FIGS. 11A-11D, the tube 32 provides the shape retaining element and is configured to affect and/or hold the shape of device 10. In one example, shown in FIG. 11A, tube 32 is pre-bent into a shape having a curvature 32a conforming to the anatomical contours of a typical user (e.g., conforming to a majority of female patients) and maintains the shape during use. In some embodiments, tube 32 is manufactured of a polyurethane material, such as McMaster Polyurethane Tubing for Water, that maintains a pre-bent shape.

In another example, tube 32 has an adjustable shape (i.e., the curvature of tube 32 is adjustable). In such an embodiment, tube 32 is flexible such that it can be manipulated by a person (e.g., a healthcare provider or a user) in various directions and is configured to retain its shape following the manipulation. The curvature of device 10 is adjustable, for example, to fit the anatomical curvature of any user. In one embodiment, shown in FIG. 11B, adjustable tube 32 is surrounded by links movable relative to one another, such that a configuration of the tube is able to be maintained once the tube 32 is bent into a particular shape. In one such embodiment, adjustable tube 32 includes linking segments 36 arranged sequentially along a longitudinal direction of adjustable tube 32. Each of the linking segments 36 has a first portion 36a, a second portion 36b, and a third portion 36c. Each portion is hollow or has at least an open portion for passing the tube 32 therethrough. The first portion 36a includes a spherically shaped body with an opening therein. The first portion 36a is connected to a second hollow portion 36b having a cylindrical shape and a passage therethrough for passing the tubing. The second portion 36b is connected to third hollow portion 36c having a semi-spherical shape and forming a hollow cup. The first hollow portion 36a (the spherical shape) of one segment is configured to fit within the hollow cup of the third hollow portion 36c of an immediately successive segment. In this way, the linked segments include a series of individual segments linked to (e.g., by snapping together) a successive individual segment, wherein each segment is able to move relative to the successive segment as the spherical first portion 36a moves within the hollow cup of the third portion 36c. In yet another example, the adjustable tube 32 is formed by the segments 36, rather than the tube 32 being surrounding the segments 36. Each one of the segments 36 defines a passage therethrough, whereby the first end of any one segment is coupled to the second end of an adjoining segment in such a manner as to form a substantially continuous passage for a fluid. In yet another embodiment, the tube 32 is coupled to the outside of an adjustable set of linked segments 36 that are hollow or solid.

In yet another example, shown in FIG. 11C, tube 32 has an adjustable shape (i.e., the curvature of tube 32 is adjustable). In such an embodiment, tube 32 is flexible such that it can be manipulated by a person (e.g., a healthcare provider or a user) in various directions and is configured to retain its shape following the manipulation. The curvature of device 10 is adjustable to fit the anatomy of any user. In one such embodiment, adjustable tube 32 includes a one or more wires 32c attached to (e.g., embedded within) a wall of adjustable tube 32. As one example, the one or more wires 32c are embedded within an inner wall of adjustable tube 32. The one or more wires 32c are configured to provide a flexibility to adjustable tube 32, which allows for manipulation by a person to adjust the shape of adjustable tube 32, and retains the shape once formed. A further example includes one or more bellows associated with the tube 32 that are capable of being shaped and conformed to the user by pressure differentials caused by the application of air flow into or out of the device through the tube 32. Air flow could inflate or deflate bellows or segments that would conform the device 10 to the anatomy of the user.

In a still further example, shown in FIG. 11D, tube 32 has an adjustable shape (i.e., the curvature of tube 32 is adjustable). In such an embodiment, tube 32 is flexible such that it can be manipulated by a person (e.g., a healthcare provider or a user) in various directions and is configured to retain its shape following the manipulation. The curvature of device 10 is adjustable, for example, to fit the anatomy of any user. In one such embodiment, adjustable tube 32 includes bellows 32d arranged sequentially along a longitudinal direction of tube 32. The bellows 32d are configured to allow a person to manipulate the shape of the adjustable tube 32 and retain the shape once formed. In some embodiments, the tube itself forms the bellows, and in other embodiments, the tube is surrounded by and/or coupled to an accessory providing the bellows.

Alternatively, in some embodiments, the tube 32 is provided separately from the adjustable, shape retaining element that allows the device 10 to be manipulated into and keep a shape (e.g., be shaped into and maintain a curved configuration for placement against the body of a patient until the configuration is adjusted). For example, a shape retaining element is provided in the center of the device 10, and the tube 32 is provided next to the shape retaining element, outside of the device 10, and so on. Any of the foregoing examples that allow for adjustability of the device can be provided separate from the tube 32.

Figures 12A, 12B, 12C:
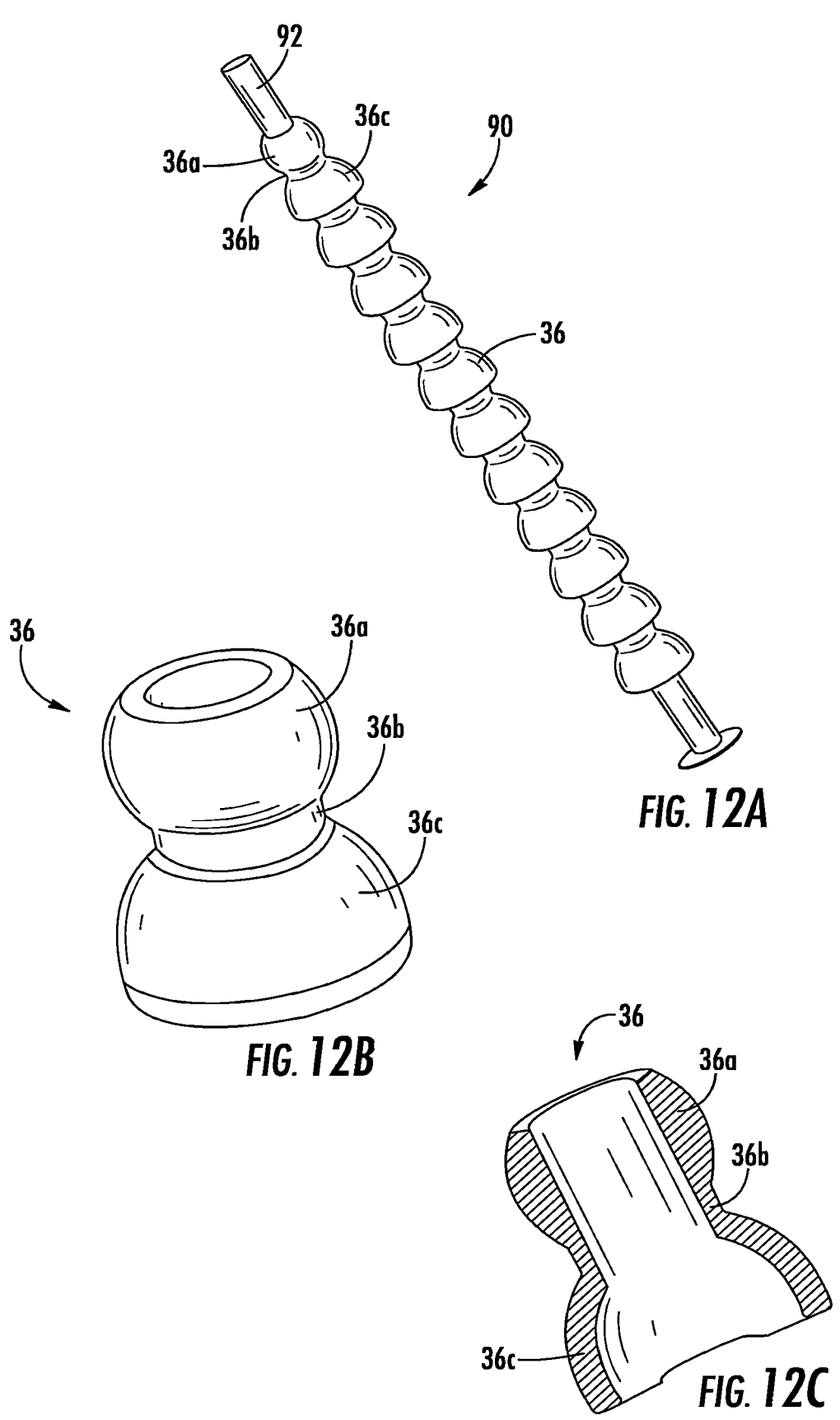
FIG. 12A is a side perspective view of a shape retaining element for a urine collection device, according to an exemplary embodiment.
FIG. 12B is a side perspective view of a linking segment of the shape retaining element illustrated in FIG. 12A, according to an exemplary embodiment.
FIG. 12C is a sectional view of the linking segment illustrated in FIG. 12B, according to an exemplary embodiment.

FIG. 12A illustrates a shape retaining element 90, according to an exemplary embodiment. In the embodiment shown in FIG. 12A, the shape retaining element 90 includes a number of linking segments 36. As shown in FIGS. 12B-C, the linking segments 36 are similar to the linking segments 36 described above with reference to FIG. 11B, including a first portion 36a with a spherically shaped body, a second portion 36b with a cylindrical shape, and a third portion 36c having a semi-spherical shape forming a hollow cup. As such, the linking segments 36 are configured to fit together by the first portion 36a of a first linking segment 36 fitting into a third portion 36c of a second linking segment 36 such that the linking segments 36 are movable relative to each other. Additionally, as further shown in FIGS. 12B-C, the linking segments 36 are hollow such that, when the linking segments 36 are connected together to form the shape retaining element 90, a solid core 92 is provided along the center of the shape retaining element 90. As such, the linking segments 36 of the shape retaining element 90 are not in fluid communication with each other.

Figures 13A, 13B, 13C:
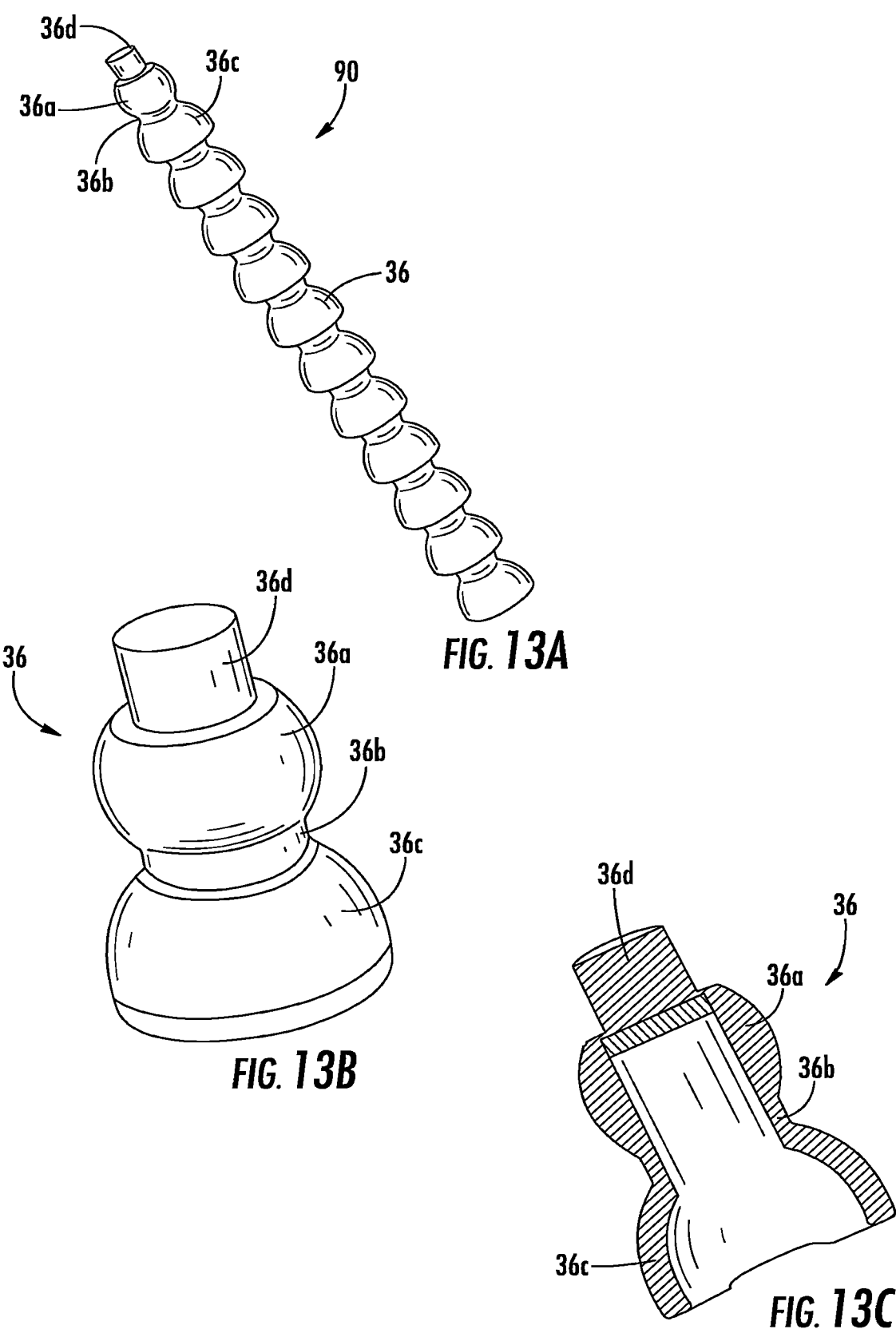
FIG. 13A is a side perspective view of another shape retaining element for a urine collection device, according to an exemplary embodiment.
FIG. 13B is a side perspective view of a linking segment of the shape retaining element illustrated in FIG. 13A, according to an exemplary embodiment.
FIG. 13C is a sectional view of the linking segment illustrated in FIG. 13B, according to an exemplary embodiment.

FIG. 13A illustrates another shape retaining element 90, according to an exemplary embodiment. In the embodiment of FIG. 13A, the shape retaining element 90 again includes a number of linking segments 36. However, as shown in FIGS. 13B-C, the linking segments 36 according to this embodiment include a cap portion 36d on top of the first portion 36a. As such, when the linking segments 36 are connected together to form the shape retaining element 90, the linking segments 36 are each closed off from each other such that, for example, the linking segments 36 of the shape retaining element are not in fluid communication with each other.

Figure 14:
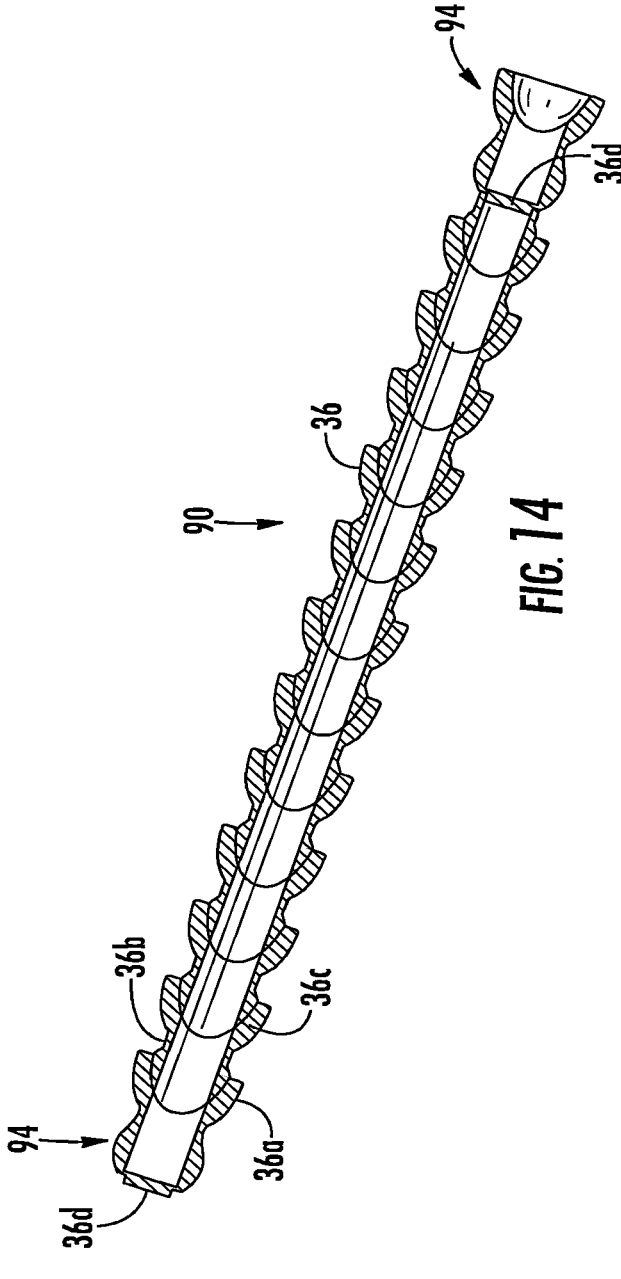
FIG. 14 is a sectional view of another shape retaining element for a urine collection device, according to an exemplary embodiment.

FIG. 14 illustrates a lengthwise cross-section of another shape retaining element 90, according to an exemplary embodiment. The shape retaining element 90 according to FIG. 14 is again formed from a number of linking segments 36 connected together. These linking segments 36 are primarily similar to the linking segment 36 shown in FIGS. 12B-C, with each linking segment 36 having a hollow first portion 36a, second portion 36b, and third portion 36c without any cap portions. However, the first and last linking segments of the shape retaining element 90 are cap linking segments 94 and are configured similarly to the linking segment 36 shown in FIGS. 13B-C, with each cap linking segment 94 also having a cap portion 36d. As such, because the cap linking segments 94 include cap portions 36d, the shape retaining element 90, as a whole, is not in fluid communication with surrounding fluids of the device 10.

Figure 15:
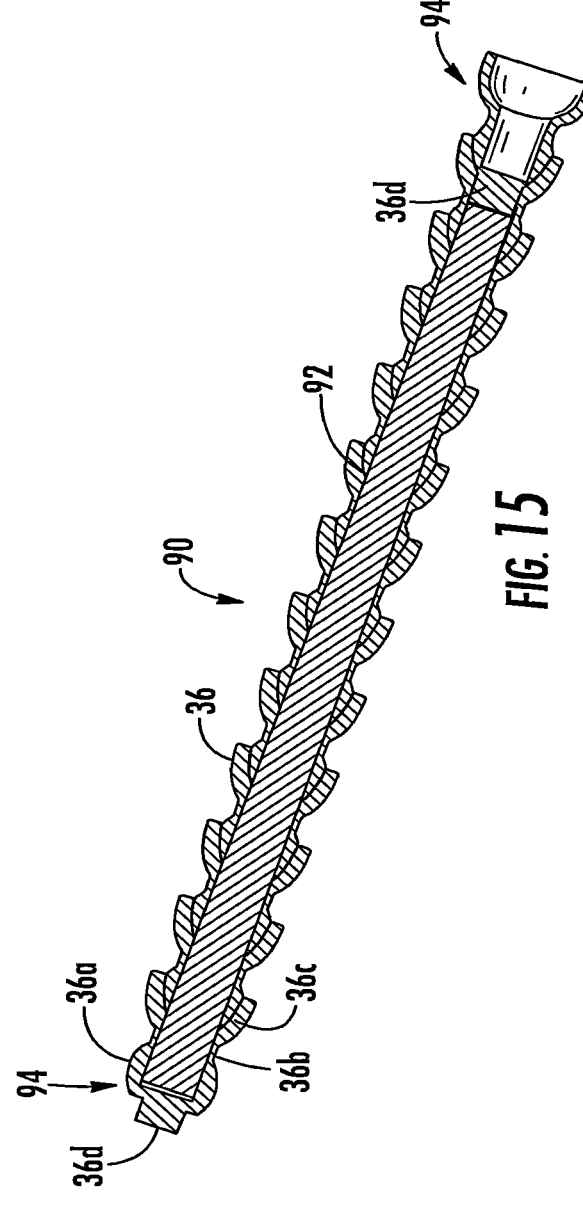
FIG. 15 is a sectional view of another shape retaining element for a urine collection device, according to an exemplary embodiment.

FIG. 15 illustrates a lengthwise cross-section of another shape retaining element 90, according to an exemplary embodiment. The shape retaining element 90 according to FIG. 15 is similar to the shape retaining element 90 shown in FIG. 14, being formed from a number of hollow linking segments 36 and capped by two cap linking segments 94. However, the center of the shape retaining element 90 is also provided with a solid core 92 extending through the hollow centers of the linking segments 36. Alternatively, in some embodiments, the core 92 is replaced with a tube (e.g., similar to the tube 32) that is thus fully contained within the shape retaining element 90. The shape retaining element 90 is provided with the core 92 or with a tube, for example, to ensure that the shape retaining element 90 is subject to "global bends," or bends extending smoothly along the extent of the shape retaining element 90, rather than "local bends," or bends extending only along localized areas of the shape retaining element 90.

FIG. 16A illustrates another linking segment 36 used to form a shape retaining element, according to an exemplary embodiment. As shown in FIG. 16A, the linking segment 36 includes a first portion 36a with a hollow spherically shaped body, a second portion 36b with a hollow cylindrical shape, and a third portion 36c having a semi-spherical shape forming a hollow cup. Additionally, third portion 36c is formed with a number of slots 36e spaced around the linking segment 36. As such, when linking segments 36 according to FIG. 16A are connected together, as shown in FIG. 16B, the linking segments 36 do not allow fluid flow (e.g., urine or air flow created by suction) between each other due to the slots 36e. In this way, the linking segments 36 are connected together to form a shape retaining element 90, as shown in FIG. 16C, that does not provide for fluid communication along the lengthwise extent of the shape retaining element 90.

Figure 17A:
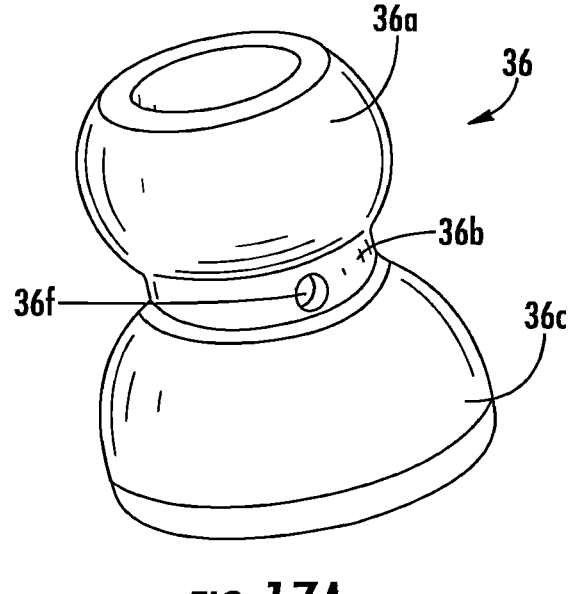
FIG. 17A is a side perspective view of a linking segment of a shape retaining element, according to an exemplary embodiment.
Figure 17B:
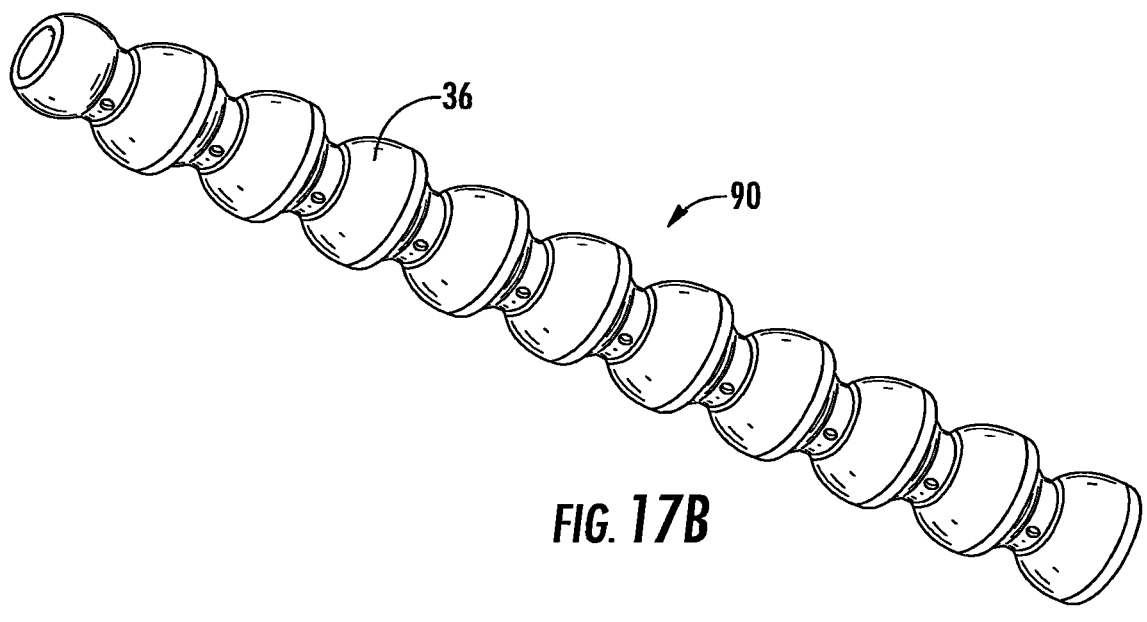
FIG. 17B is a side view of a shape retaining element formed from multiple linking segments illustrated in FIG. 17A, according to an exemplary embodiment.

FIG. 17A illustrates another linking segment 36 used to form a shape retaining element, according to an exemplary embodiment. As shown in FIG. 17A, the linking segment 36 includes a first portion 36a with a hollow spherically shaped body, a second portion 36b with a hollow cylindrical shape, and a third portion 36c having a semi-spherical shape forming a hollow cup. Additionally, the second portion 36b is provided with one or more holes 36f. As such, when the linking segments 36 according to FIG. 17A are connected together to form a shape retaining element 90, as shown in FIG. 17B, the linking segments 36 do not allow fluid flow (e.g., urine or air flow created by suction) between each other due to the holes 36*f*.

Figures 18A, 18B, 18C:
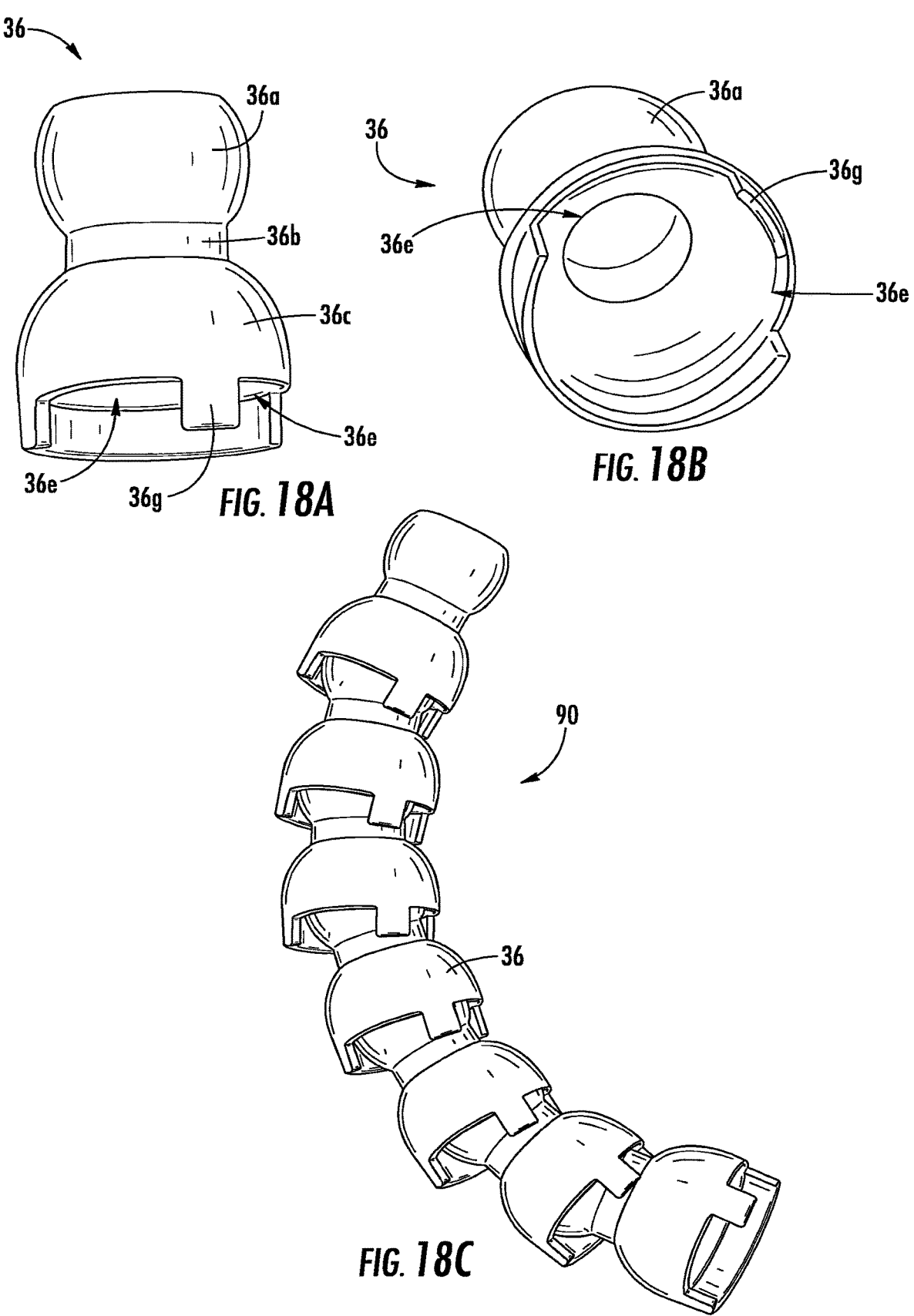
FIGS. 18A-B are side perspective views of a linking segment of a shape retaining element, according to an exemplary embodiment.
FIG. 18C is a side view of a shape retaining element formed from multiple linking segments illustrated in FIGS. 18A-B, according to an exemplary embodiment.
Figure 18D:
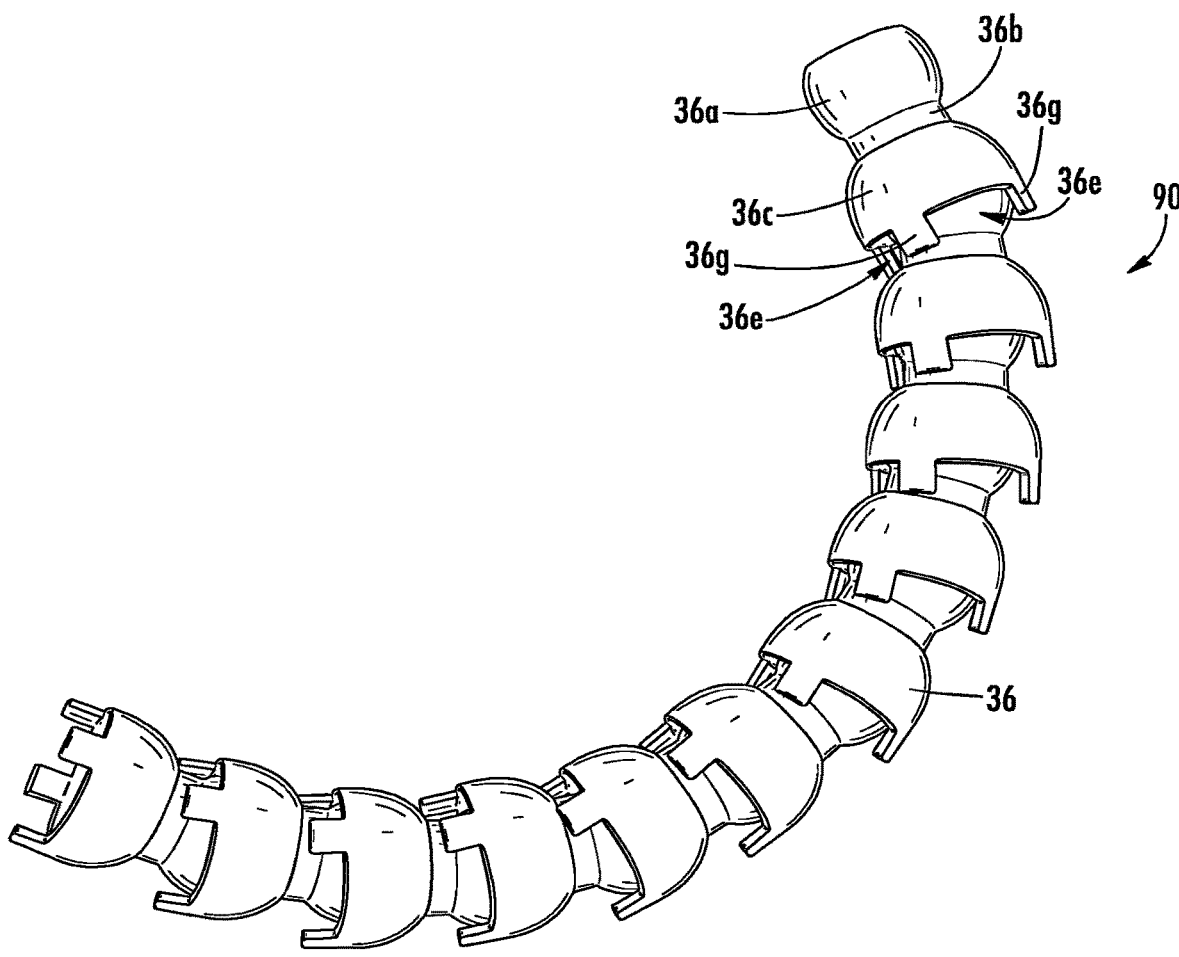
FIG. 18D is a side view of another shape retaining element, according to an exemplary embodiment.

FIGS. 18A-B illustrate another linking segment 36 used to form a shape retaining element, according to an exemplary embodiment. As shown in FIGS. 18A-B, the linking segment 36 includes a first portion 36*a* with a hollow spherically shaped body, a second portion 36*b* with a hollow cylindrical shape, and a third portion 36*c* having a semi-spherical shape forming a hollow cup. However, the third portion 36*c* is provided with two slots 36*e* forming a member 36*g* between them. As such, one side of the linking segment forms a flange while the other side is largely open. Due to this, the linking segments 36 according to FIGS. 18A-B are connected together to form a shape retaining element 90 that allows for a one-way bend because the flanged side of the linking elements 36 blocks a backwards bend. Moreover, the members 36*g* facilitate a global bend along the shape retaining element 90 by allowing for a uniform radius of curvature. In some embodiments, the ends of the shape retaining element 90 are closed off (e.g., by being provided with linking segments including cap portions 36*d*). Additionally, as shown in FIG. 18D, the linking segments 36 are provided with a larger number of slots 36*e* creating a larger number of members 36*g* such that the shape retaining element 90 is bendable in more than one direction.

It should be understood that the shape retaining elements 90 illustrated in FIGS. 12-18 are exemplary and that other shape retaining elements 90 may instead be used with a urine collection device. For example, a flexible tube or solid element may be impregnated with or be wrapped in a coiled foil or mesh made up of a thin flexible metal to form a shape retaining element 90, with the coiled foil or mesh configured to be flexible and hold the shape of the element 90 when bent. As another example, the coiled foil or mesh is used by itself as a shape retaining element 90. The flexible mesh or element may be molded into the flexible tube or flexible solid element such as by co-extrusion.

In some embodiments, the device 10 is otherwise configured to conform to the curvature of the user and to maintain its shape while in use. In one example, the device 10 or the tube 32 may be constructed with a bias to a curved configuration. The bias is provided, for example, by a spring, or by one or more memory shaped wires or supports associated with the device 10 or the tube 32. In this way, the device 10 is naturally inclined to a curved position, optionally, a tight curvature. For positioning on the user, the device 10 can be "opened" or otherwise straightened, and then released when placed in a proper location, thereby held tightly against the user's body in a conformed configuration by the biasing force.

In another example, a device is individually configured to a user to provide a custom fit. This is achieved, for example, through curation of a polymer after setting the device to a proper fit for the user. As an example, a molded plastic part is warmed such that the proper shape can be set as it cools in a proper position on the user. In another example, an external light source assists with curing the device to have a custom fit.

In yet another example, the application of suction can also be used to shape and conform the device to the user by creating vacuum. For example, once the suction is turned on, the reduced pressure created within the device body can draw in or otherwise act upon the body to move it to a curved configuration that corresponds with the user's anatomy. In some embodiments, the device includes one or more bellows capable of being shaped and conformed to the user by pressure differentials caused by air flow into or out of the bellows. Air flow could inflate or deflate bellows or segments that would conform the device 10 to the anatomy of the user. Similarly, in other embodiments, the reduced pressure created in the cavity of the device holds and maintains the unit in place, in addition to being useful for conforming to the wearer's body. In this way, the use of suction may draw in or otherwise engage the device 10 with the user's body.

Figure 19:
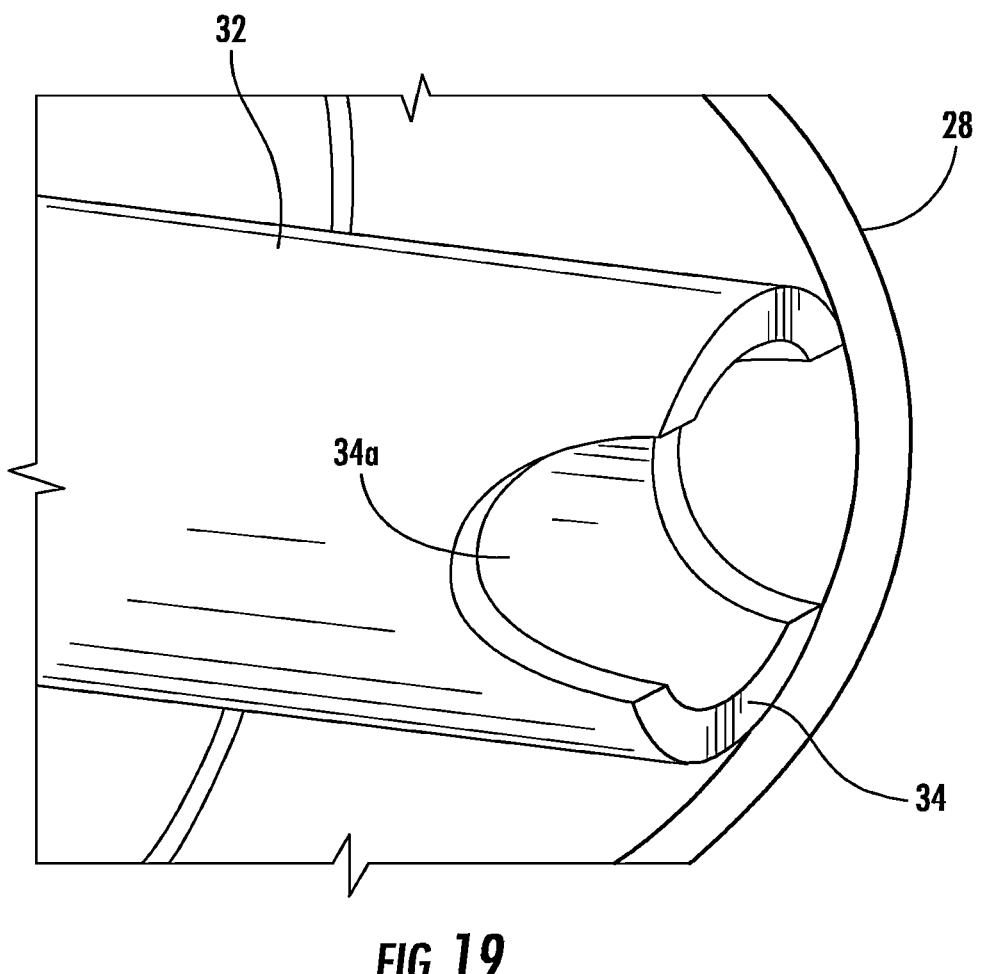
FIG. 19 is an enlarged view of an end of a tube of a urine collection device disposed in a cap, according to an exemplary embodiment.

As shown in FIG. 19, according to an exemplary embodiment, the second end 34 of the tube 32 has a slit, aperture, or cut out portion, such as aperture 34*a*, to better allow air flow into the cap 28 while the suction is applied. The space created between the second end 34 of the tube 32 and the cap 28 by the slit, aperture, or cut prevents the second end 34 from being suctioned to and forming an air tight seal against the cap 28, which would prevent the flow of the collected urine through the tube 32.

Figure 20:
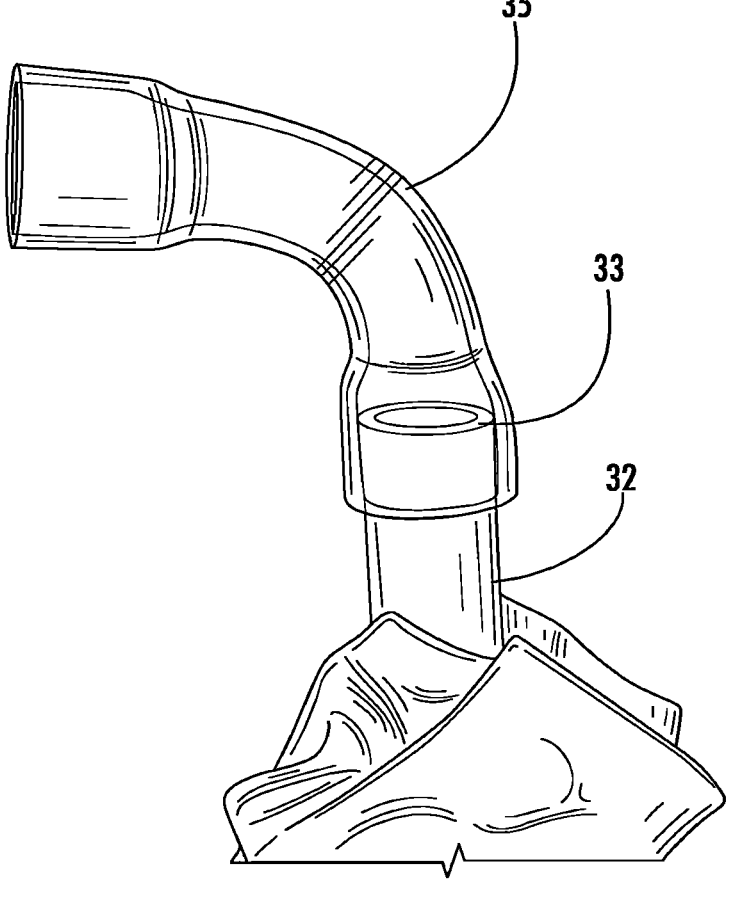
FIG. 20 is a side view of a curved tube extension of a urine collection device, according to an exemplary embodiment.
Figure 32:
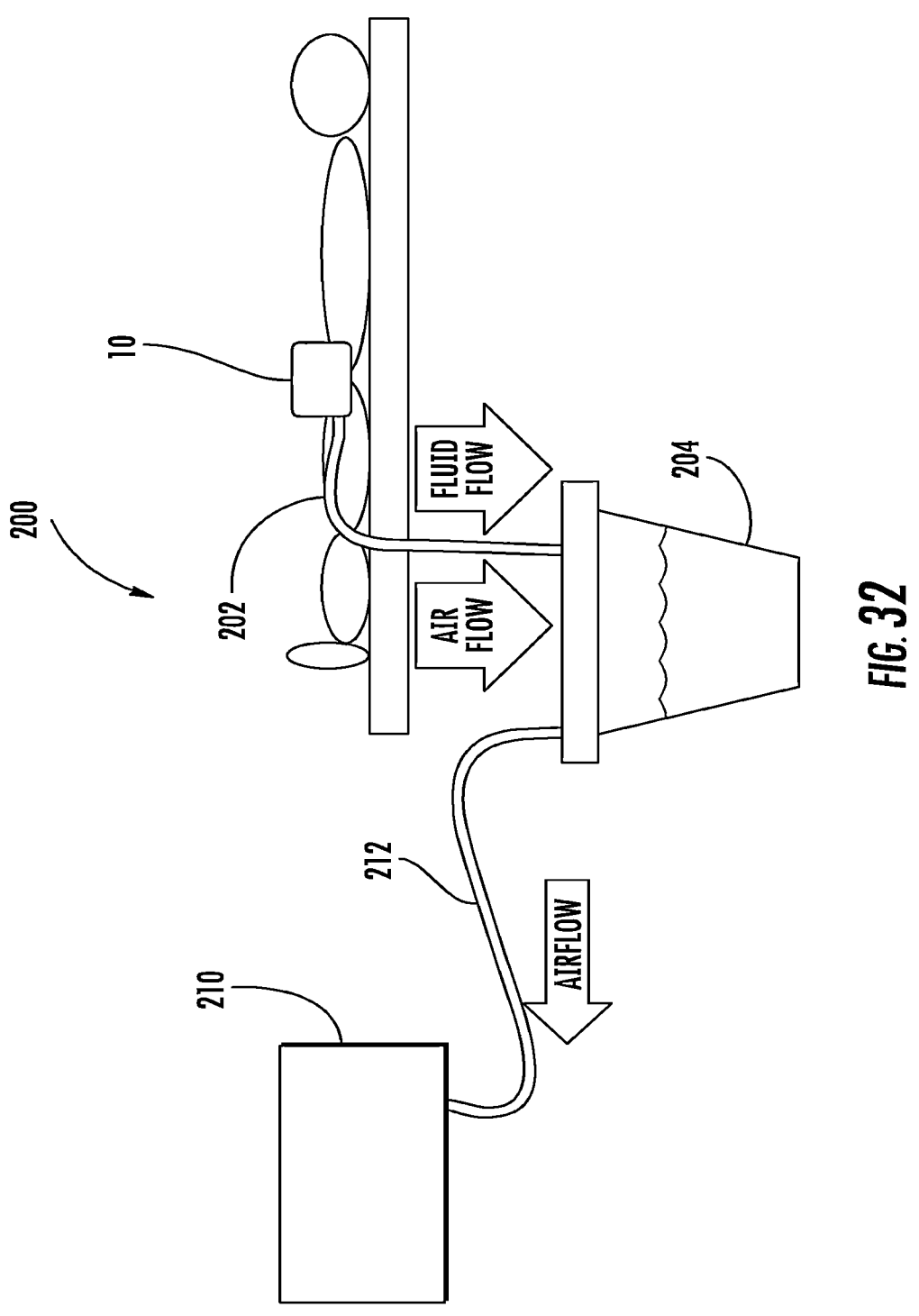
FIG. 32 is a schematic diagram of a urine collection system according to an exemplary embodiment.

In some embodiments, the tube 32 extends all the way from the device 10 to a fluid collection reservoir 204, as depicted in FIG. 32 and described in further detail below. However, in other embodiments, tube 32 terminates at the first end 33 of the tube, and is coupled at the first end 33 to a curved tube extension 35, as shown in FIG. 20. In such embodiments, the curved tube extension 35 is an intermediate element between the tube 32 and a discharge tube line 102 that is coupled between the device 10 and the collection reservoir 204 as shown in FIG. 32. The curved tube extension 35 is used to modify the direction at which the tube 32 and discharge tube line 202 extend. It is advantageous that the tubing be directed away from the user's body, such as off the side of the bed, rather than extending up towards the head of the user. This prevents the tubing from accidental pulling, risking leakage by pulling the device out of its placement in relation to the urethral opening of a user, or being an irritation to the user. Accordingly, the curved tube extension 35 directs the tubing immediately off to the side of the user, without causing a bend and possible kink in the tube which may occur when attempting to bend a straight tube. In some embodiments, the first end 33 of the tube 32 is formed to have a curvature making the bend, thereby eliminating the need for a separate curved tube extension 35 element.

In some embodiments, the curved tube extension 35 is capable of rotation relative to the first end 33 of the tube 32 so a user or another person disposing the device on the body of a user is able to direct the tubing to extend in any direction, for example, in a preferred direction depending on where the collection reservoir is placed relative to the user.

Referring again to FIGS. 1-7, the urine collection device 10 further includes cap 28 at the open second end 24 of the external covering 20. Cap 28 is coupled to the second open end of the external covering 20, and a water-tight seal is formed therebetween. Cap 28 acts as a reservoir for diverted fluid which has been collected by the device 10 from the urethral opening of a user. As described above, the second end 34 of the tube is disposed in the cap 28, such that fluid is drawn through the tube 32 from within the cap 28. In some embodiments, cap 28 has an outer surface configured to secure the device in position relative to the user, i.e. between the gluteal folds within the perineum. In some embodiments, the cap 28 is sized and configured to hold together the ends of the tube 32, the inner collection core 42, and the outer collection layer 40 such that the urine collected and drawn through the inner collection core 42 and outer collection layer 40 is diverted (i.e., due to gravity or a reduced pressure created in the cap by suction through the tube 32) and collected in the cap 28. The cap 28 is configured to collect and hold urine that has been expelled from the urethral opening of a user for a temporary period of time until the urine is removed from the device through the tube 32. In some embodiments, the cap 28 is any suitable shape and/or size capable of collecting fluid removed from the urethral opening of a user and passed through the outer collection layer 40 of the device 10.

Figure 21A:
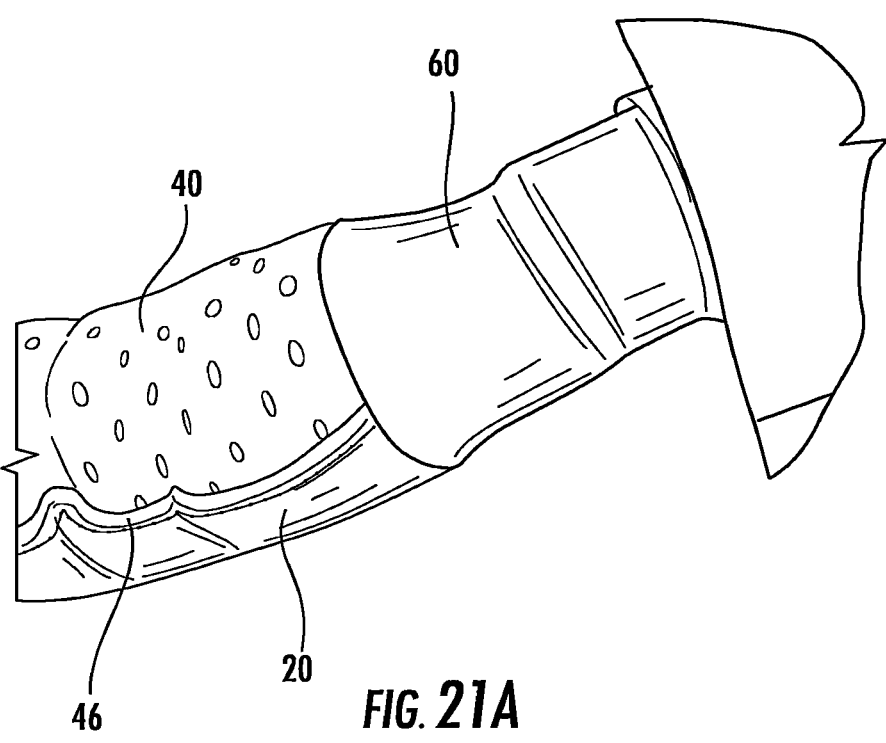
FIGS. 21A-B depict another embodiment of a urine collection device.
Figure 21B:
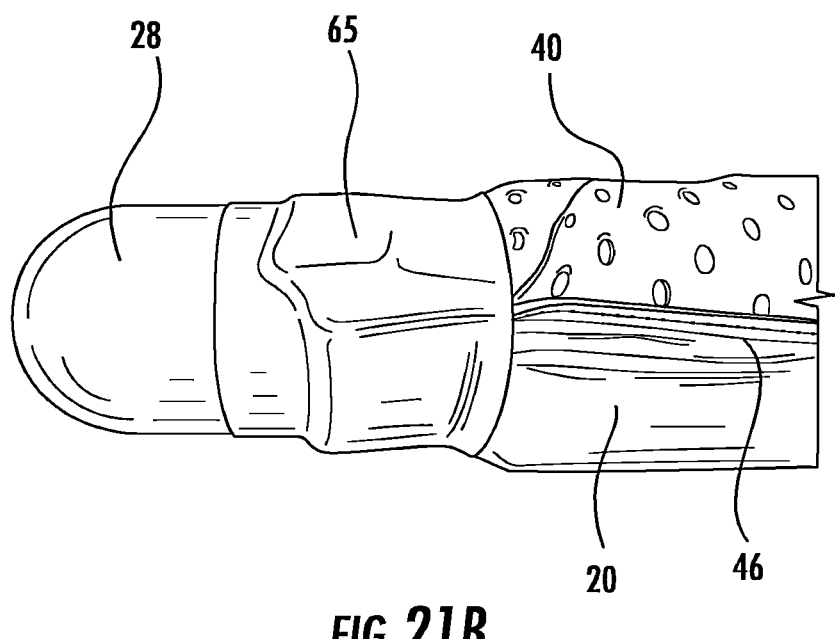

Cap 28 is attached to device 10 by any suitable means. In one example, cap 28 is attached (e.g., secured, connected, etc.) to the open second end 24 of device 10 by tape. In a further example, as shown in FIG. 21B, cap 28 is attached or connected to the open second end 24 by shrink wrapping 65 wound around cap 28 and the open second end 24, thus securing cap 28 to the open second end 24 of device 10.

In some embodiments, cap 28 has a cup-like shape. In some embodiments, cap 28 is manufactured of a material that is biocompatible (e.g., will not induce an immune response in a user), soft so as not cause pressure points, and/or flexible. Cup-shaped cap 28 is, for example, formed of silicone rubber or other polymeric material which may be certified as USP Class-IV.

Figure 22:
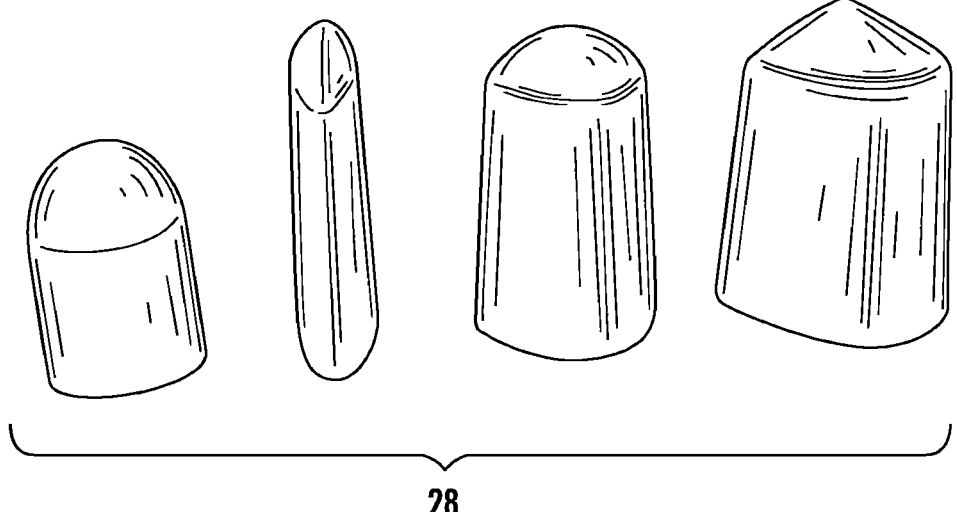
FIG. 22 depicts various alternative exemplary embodiments of a cap of a urine collection device.

In some embodiments, cap 28 has a wedge shape, as shown in the various embodiments illustrated in FIG. 22. A wedged-shaped cap has a cup portion with a tapered surface configured to fit into the gluteal folds and perineum of the body of a user such that cap 28 stays in position on the body of a user.

In some embodiments, an external portion of the cap 28 has an adhesive portion. The adhesive portion is configured to secure device 10 to the body of a user between the gluteal folds such that device 10 stays in position on the body of a user. In some embodiments, the adhesive portion is made of any suitable biocompatible material (e.g., does not induce an immune response in a user). For example, the adhesive portion is made of a silicone based adhesive with certifications for cytotoxicity, skin irritation, and skin sensitization. The adhesive portion may be an adhesive coating or material applied to the exterior of the cap 28, or may be a piece of adhesive material adhered to the exterior of the cap 28.

Figure 23A:
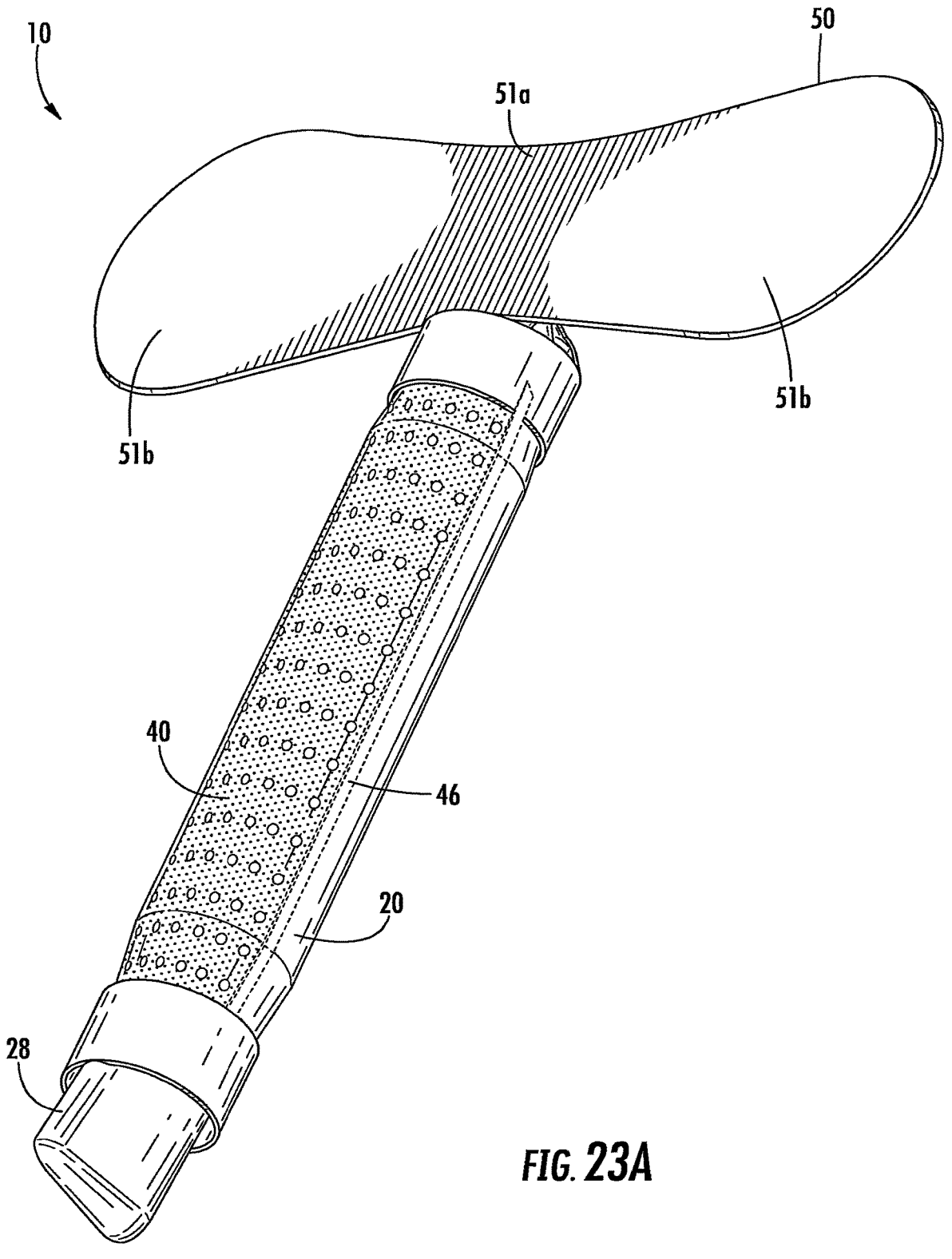
FIGS. 23A-B depict another embodiment of a urine collection device.
Figure 23B:
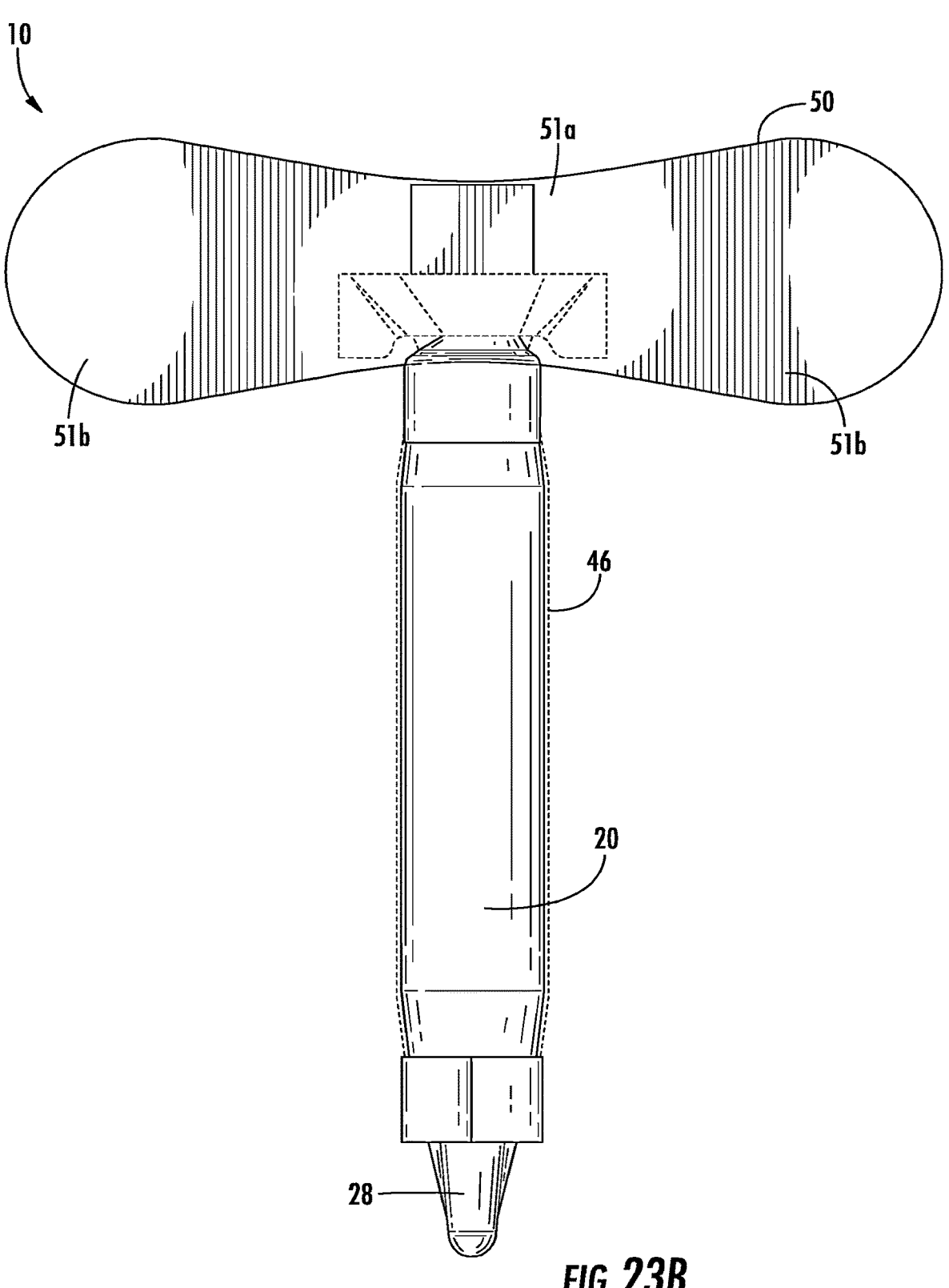

Referring again to FIGS. 1-7, the urine collection device 10 includes an anchor 50 connected to the device 10 at or adjacent to the open first end 22 of the external covering 20. The anchor 50 is configured to secure the device 10 in position to collect and transport urine voided by a user. The shape of the anchor 50 is configured to conform to the surface area of the skin of the pelvic region of the user without pulling or pinching the skin or bunching up in ways that would cause discomfort. Anchor 50 has any suitable shape and structure to secure the device to the body of a user and to remain secured despite a wearer's motion, moisture accumulation on the body, or passage of time. In the embodiment shown in FIGS. 1-7, anchor 50 includes a center portion configured to attach to the body of a user between the pubic region and the umbilical region, with two wing portions extending outward towards the lateral regions of the body. In another embodiment, as shown in FIGS. 23A-B, anchor 50 has a shape extending in a more lateral manner relative to the device, having a narrower central portion 51a and wider wing portions 51b on each side of the central portion 51a. In this embodiment, the anchor 50 is particularly suited for the specific patient, depending on age, weight, body composition, or other factors that may dictate the size of the anchor 50. For example, the laterally extending anchor 50 in FIGS. 23A-B may provided in a first size (up to approximately 5 centimeters in length), a second size (between approximately 5 centimeters and 15 centimeters in length), a third size (between approximately 15 centimeters and 25 centimeters in length), and/or a fourth size (between approximately 25 centimeters and 40 centimeters in length). Similarly, the laterally extending anchor 50 in FIG. 23A-B may be provided having different widths, for example a first size (up to approximately 2 centimeters wide), a second size (between approximately 2 centimeters and 6 centimeters wide), a third size (between approximately 6 centimeters and 10 centimeters wide, and/or a fourth size (between approximately 10 centimeters and 20 centimeters wide). A health care professional may have a variety of anchors from which to choose from in the above ranges, and may select the anchor most appropriate for the user.

Figure 24:
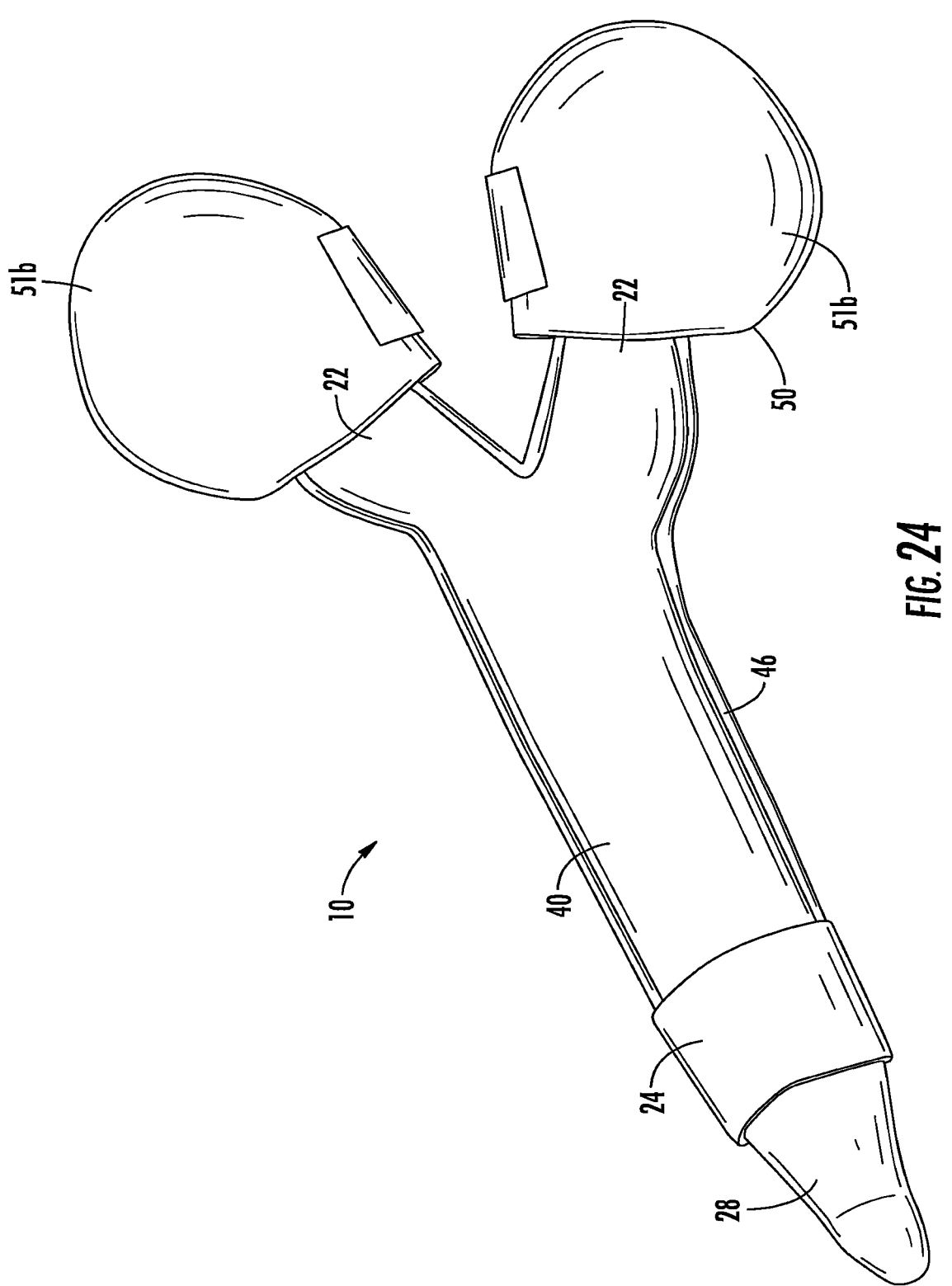
FIG. 24 depicts another embodiment of a urine collection device.

Alternatively, the anchor 50 includes wider portions that are not connected by a central portion. As an illustration, FIG. 24 depicts an embodiment of a urine collection device 10 designed such that a body of the device 10 bifurcates into two ends 22 (e.g., into a "Y" shape), and each end is provided with a wider portion 51b. Accordingly, the two wider portions 51b move independently from each other. Such a design may allow for a more customized fit to a patient, as the bifurcations and separate portions 51b allow the device 10 to be more flexibly fitted to a patient in placing the device 10 due to more degrees of freedom.

In some embodiments, anchor 50 includes an external film for covering an adhesive layer, which is configured to be easily removable using a tab or tabs that are part of the external film or are connected to the external film. In some embodiments, anchor 50 further includes a tab configured to allow a person (e.g., a healthcare provider) to remove the anchor 50 from the body of a user without causing discomfort or harm to the body of a user when attempting to remove. The anchor 50 and adhesive layer may be of such a configuration to avoid portions of the body that are covered with hair, since adhering the anchor to these portions of the body could result in uncomfortable pulling or removing hair upon removal of the anchor 50. According to some embodiments, only a portion of the anchor 50 includes adhesive for securing to the user. For example, only the outer edges of the anchor 50 include an adhesive area, or only the inner areas not extending to the outer edges include the adhesive area. In yet another example, only certain portions or plots within the anchor 50 area include adhesive. Various configurations and placement of adhesive may be used to best accommodate securing the anchor 50 and the device 10 to the user's body without over-use of adhesive.

According to some embodiments, the anchor 50 is constructed having separate and removable portions, such that the anchor 50 has a variable shape and/or dimension. For example, the anchor 50 has perforations such that certain distal portions or entire areas of the anchor 50 can be removed to better fit the body of the user. The anchor 50 is, alternatively, adjustable to allow for varying the dimension of the anchor.

The anchor 50 may be any suitable biocompatible material which may be used with the skin of a user, such as human skin. In some embodiments, anchor 50 is stretchable. In some embodiments, anchor 50 is manufactured of a urethane or other polymeric material film adhesive having a foam backing configured to provide strength, stability, and support. For example, the adhesive layer is silicone based with a minimal amount of acrylic or none at all. In some embodiments, the adhesive is a Dow Corning Soft Skin Adhesive MG 7-9900. In some embodiments, the foam backing provides a layer to prevent the tube 32 from rubbing against the skin adjacent to the pelvic region of the user.

Anchor 50 is attached to device 10 by any suitable means. In one example, anchor 50 is attached (e.g., secured, connected, etc.) to the open first end 22 of device 10 by tape that secures anchor 50 to open first end 22. In a further example, as shown in FIG. 21A, anchor 50 is attached or connected to the open first end 22 by shrink wrapping 60 wound around an end of anchor 50 and the open first end 22, thus securing anchor 50 to the open first end 22 of device 10.

In other embodiments, the anchor portion is provided for use in association with the device 10, but that is not directly coupled to the device 10. For example, an adhesive portion is provided to secure the tube 32 or discharge tube line 102 to the user, but not necessarily to secure the device 10 itself to the user. In another embodiment, an anchor 50 as described above may be provided with the device 10, but that is not directly coupled to the device 10 during production. In yet another embodiment, the device does not include anchor 50 at all, and is able to be fixed relative to the body by another fixation mechanism exemplified below.

For example, in addition to or instead of anchor 50, the device 10 includes another fixation mechanism such as an elastic band or strap. In this example, the band or strap is coupled to the device 10 and configured to wrap around the user's waist or leg, for example. Similarly, the device 10 may be configured to be used in association with a wearable garment, such as a brief that is used to hold the device 10 in position relative to the user's body. In yet another example, a projection extends from the device 10 that is configured to be inserted into the vagina of the user to maintain the positioning of the device 10.

As mentioned previously, in some embodiments, the cap 28 also provides for fixation of the device relative to the body. Referring again to FIG. 22, the various shapes of the cap 28 provide for associating the device with the body in a more secure relationship. For example, the wedge-shaped cap 28 shown in the embodiment of FIGS. 23A-B fits with the anatomy, such as in the gluteal folds, the gluteal cleft, or the perineum. In this way, the device 10 is more securely fixed relative to the body. In some embodiments, the cap 28 also has adhesive on the outer surface to increase the fixation even further. In some embodiments, the device 10 includes an additional adhesive area, either along the sides or the distal end of device 10 to assist with fixation. The additional adhesive area may be a second anchor configured for attachment to the user's body. The additional adhesive area may also be located along the sides of the device 10. The additional adhesive area may be used instead of anchor 50 and/or cap 28 adhesive, or may be used in combination with one or both.

Finally, as mentioned previously, the application of the suction may be used to hold the device 10 securely in place on the user's body. For example, the suction may be used to form the device 10 in a curvature corresponding to the user's anatomy in such a tight way that the engagement of the device 10 with the body is secure. In another example, the pressure differential between the inside of the device 10 and the ambient air surrounding the user causes the device 10 to be drawn in towards, and in direct contact with the skin of the user, which may be maintained securely until the suction creating the vacuum condition is inactivated.

In some embodiments, the device 10 also includes a wedge formed at or near open first end 22 of device 10 in an area intended to be positioned near the urethral opening of the patient. The wedge is configured to separate the labia majora and labia minora of the body of a user to maintain and direct fluid flow directly to the device 10 surface from the urethral opening. In some embodiments, shown for example in FIG. 25A, the wedge includes an orifice with a cylindrical shaped protuberance configured to fit over the urethra of the body of a user such that fluid flow is diverted from urethral opening through an internal cavity of device 10 and into cap 28. In some embodiments, shown for example in FIG. 25B, the wedge is manufactured of a fabric and configured to be disposed over the urethral opening of the body of a user and collect fluid voided from the urethral opening of the user. In yet another embodiment, shown for example in FIG. 25C, a urethral funnel 80 is disposed over the urethra of a user. The urethral funnel includes a backsplash that redirects voided fluid to a tube configured to evacuate fluid at a recess within the tube.

According to some embodiments, such as the embodiment of FIGS. 21A-B, 23A-B, and 24, external covering 20 does not form a cylindrical body as shown in the embodiments of FIGS. 1-7, and is alternatively a fluid impermeable backing formed by a sheet of fluid impermeable material wrapped around an underside of the fluid collection assembly (i.e., around a portion of the inner collection core 42 and outer collection layer 40). The fluid impermeable material may be enclosed around the fluid collection assembly on each end by tape or by shrink wrap material as described above. In this embodiment, a portion of the external covering 20 is attached (e.g., secured, connected, etc.) to outer collection layer 40 by any suitable means. For example, as shown in FIGS. 21A-B, 23A-B, and 24, edges of the external covering 20 are secured to the outer collection layer 40. In one specific example, edges of external covering 20 are sewn to the outer collection layer 40 along line 46. In another specific example, edges of external covering 20 are ultrasonically welded to the outer collection layer 40 along line 46. Accordingly, in such embodiments, the fenestration for receiving urine includes the top portion of the device 10 not covered by the external covering 20 (e.g., the top half of the device 10 shown in FIGS. 23A-B).

Figure 26A:
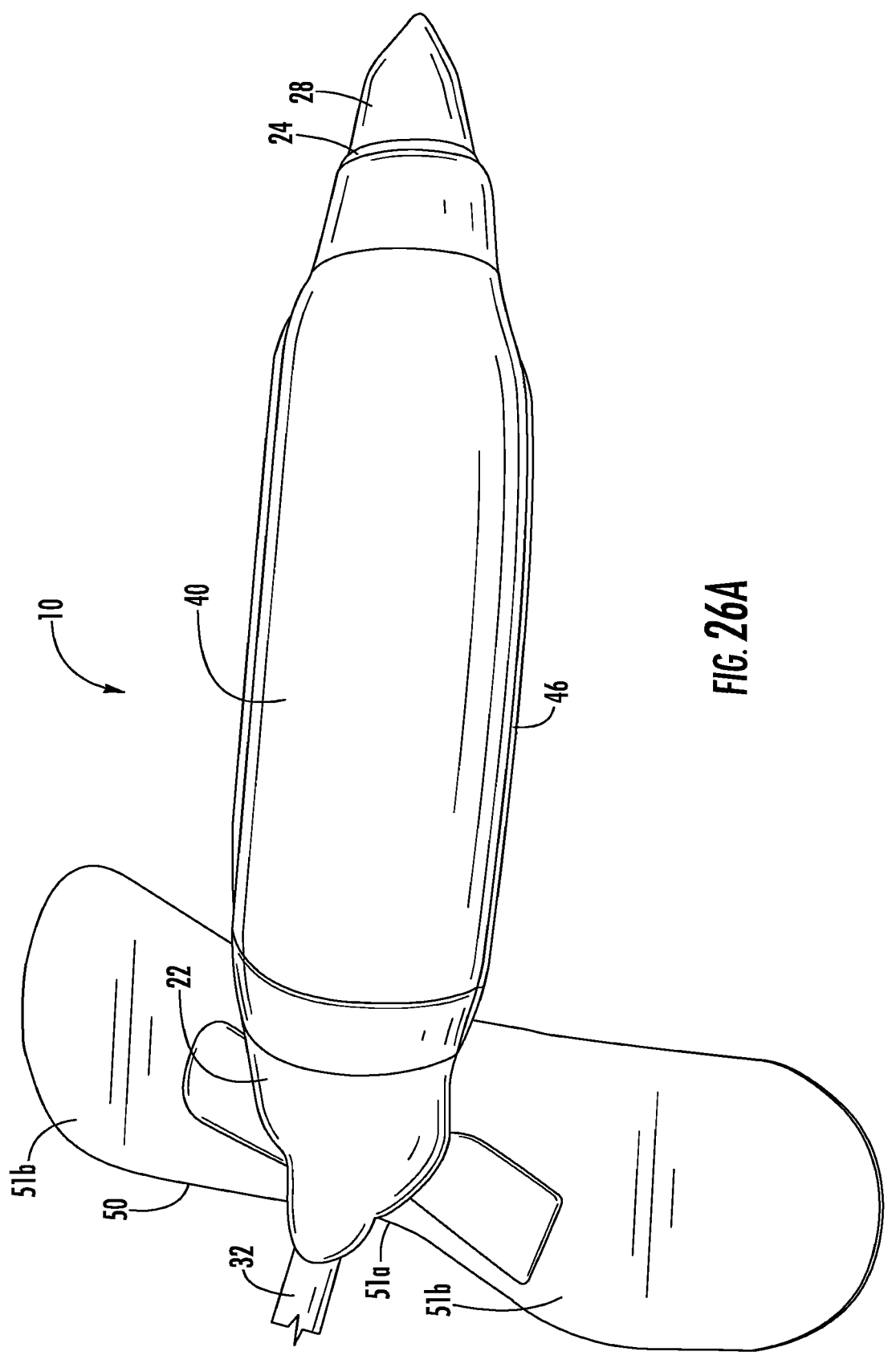
FIG. 26A depicts another embodiment of a urine collection device.
Figure 26B:
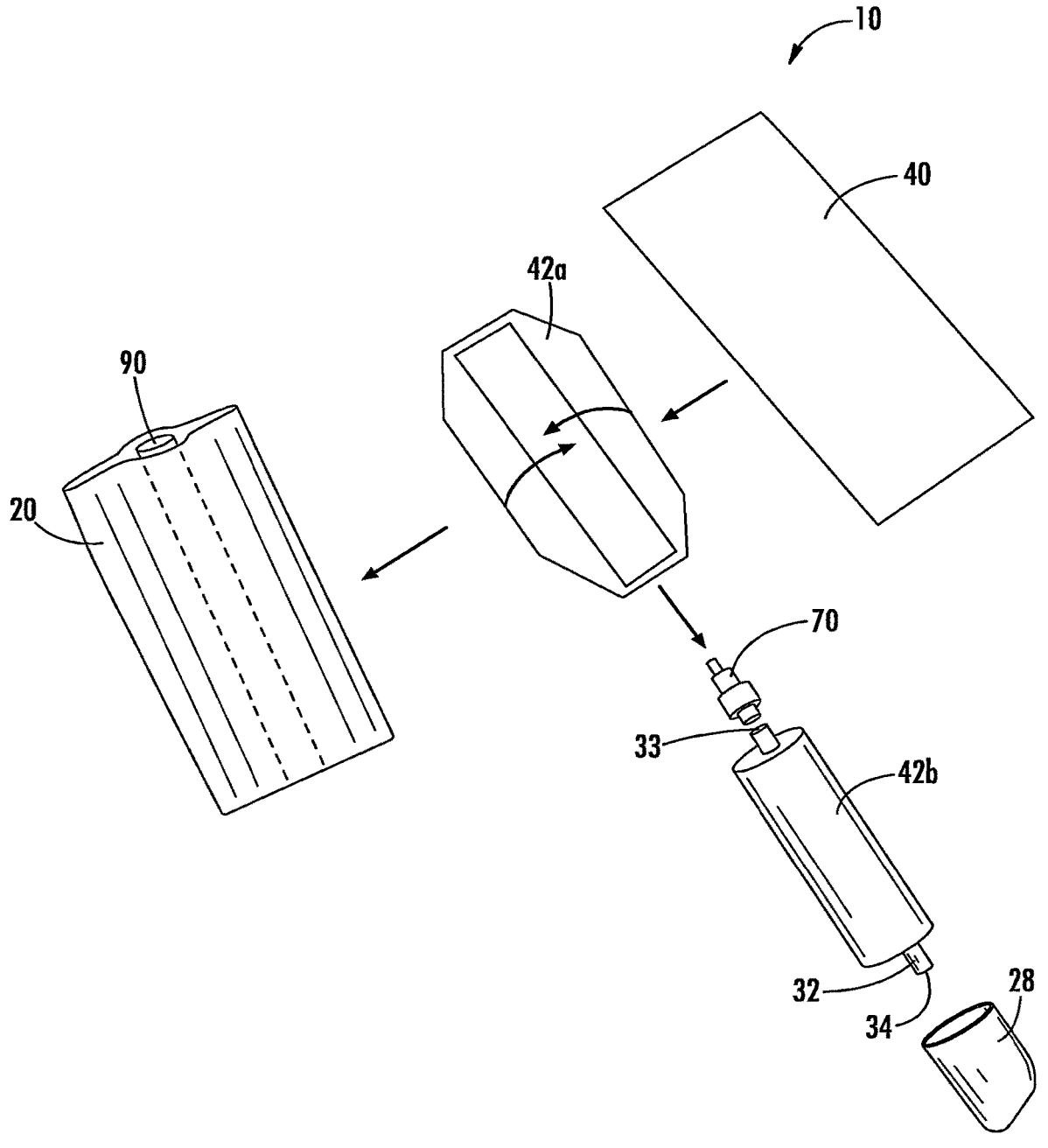
FIG. 26B is a perspective view of an exploded assembly of the device illustrated in FIG. 26A.

FIG. 26A illustrates another embodiment of the urine collection device 10 with a fluid impermeable backing. Additionally, the device 10 shown in FIG. 26A is flatter and wider than the device 10 shown in FIGS. 23A-B. As illustrated in an exploded view of the device 10 shown in FIG. 26B, the device 10 includes similar components in the fluid collection assembly of the device 10 as those shown in FIGS. 1-7. Accordingly, the device 10 shown in FIGS. 26A-B includes a collection layer 40 (e.g., created from a permeable fabric) provided on the top side of the device 10, an external covering 20 configured as a fluid impermeable backing, and a cap 28 (e.g., with a smooth bottom for a close fit to the patient's anatomy). The inner collection core 42 is provided as a first layer 42a of batting that surrounds a second layer 42b of batting, which in turn surrounds the tube 32. The device 10 also includes a suction tubing adaptor 70 that allows the tube 32 in the device 10 to be fitted to a separate length of external tubing, such as suction tubing, or another device, such as a suction device.

Further, the fluid impermeable backing includes a shape retaining element 90 provided in the form of a core integrated into the backing. In various embodiments, the core is a metal core (e.g. aluminum, lead, copper, stainless steel, or any type of soft metal) or a plastic core. For example, in one embodiment, the core of the shape retaining element 90 includes one or more shape memory wires configured to provide a bias to the device 10. As shown, the device 10 includes one shape retaining element 90, though in other embodiments the device 10 includes more than one shape retaining element 90 (e.g., two or more). The shape retaining element 90 is incorporated into the external covering 20, for example, by wrapping or encasing the shape retaining element. In some arrangements, the shape retaining element 90 is integrated into the external covering 20 by encasing the shape retaining element 90 in foam of the external covering 20. In other arrangements, the shape retaining element 90 is insulated or heat shrink dipped and incorporated into the external covering 20. It should be understood, however, that the device 10 may be formed into a different shape and/or include a different shape retaining element 90. For example, the device 10 may be formed into a Y-shape, similar to the device 10 shown in FIG. 24, with a similar Y-shaped shape retaining element 90 formed into the external covering 20.

Figure 27A:
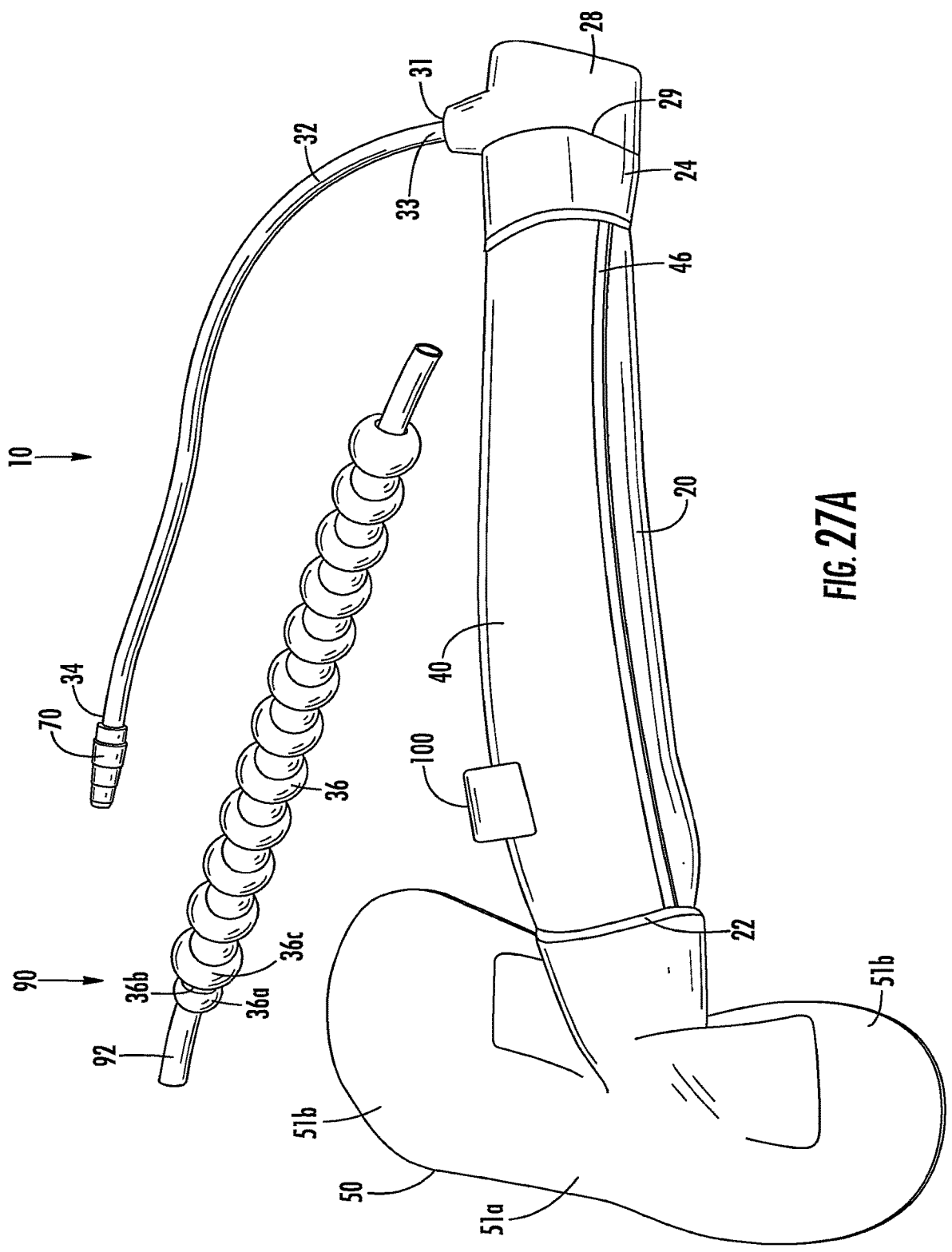
FIGS. 27A-B depict another embodiment of a urine collection device.
Figure 27B:
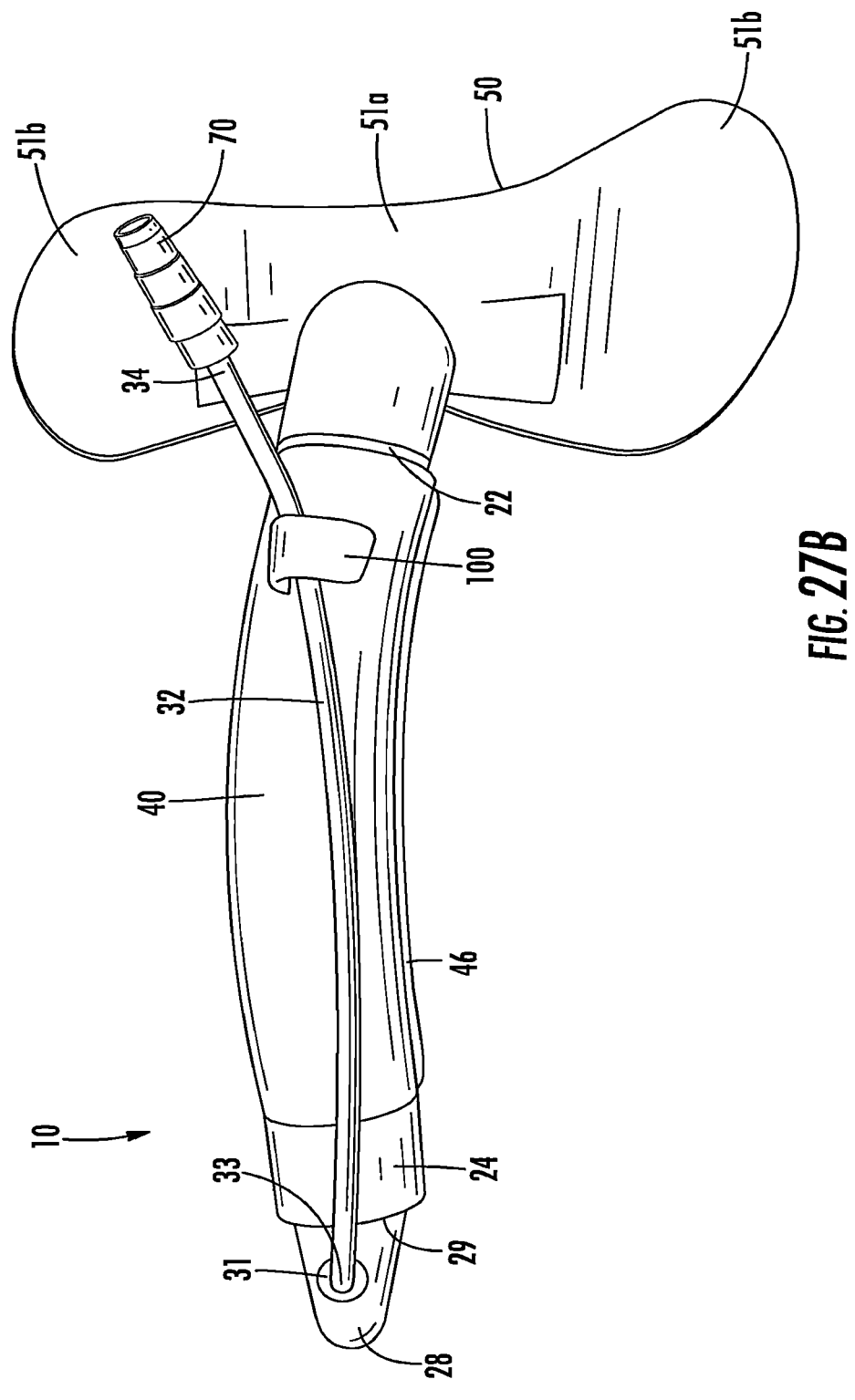
Figure 27C:
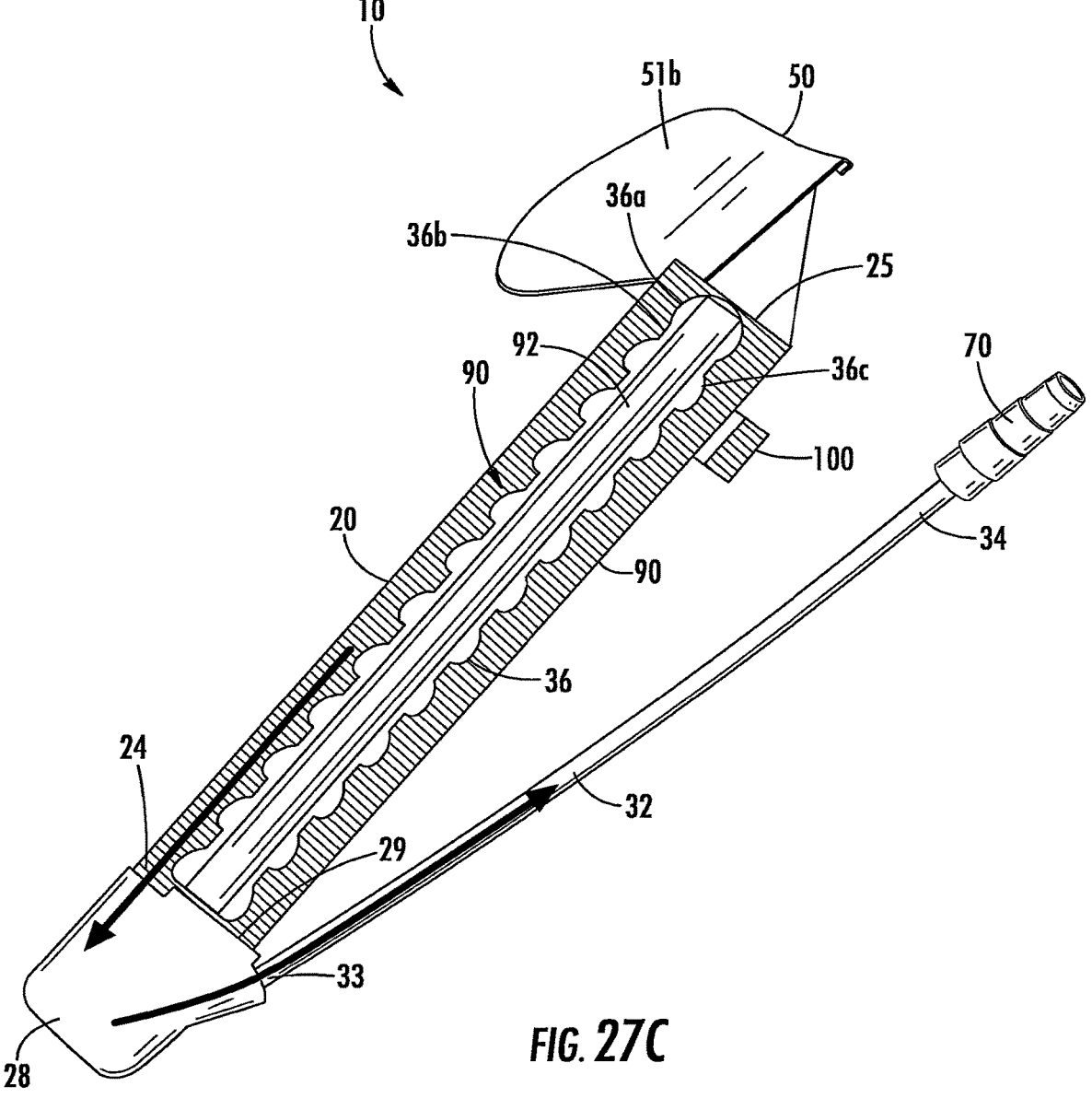
FIG. 27C depicts a sectional view of the device illustrated in FIGS. 27A-B, according to an exemplary embodiment.

FIGS. 27A-B illustrate another embodiment of the urine collection device 10 with a fluid impermeable backing. As shown in FIG. 27A, the device 10 includes a shape retaining element 90 formed from hollow linking elements 36 provided with core 92 (e.g., in the form of a tube, as illustrated in FIG. 27A, or as a solid core). As illustrated in FIG. 27C, the shape retaining element 90 is inserted into a center of the device 10 to allow the device 10 to be shaped and maintain its shape, as described above with reference to FIGS. 12-18. The core 92 is configured to support the device 10 rather than facilitate the removal of fluid from the device 10. It should further be understood that the device 10 may be provided with any of the shape retaining elements 90 described above with reference to FIGS. 12-18.

Moreover, the device 10 shown in FIGS. 27A-C includes an external tube 32 that fits into and extends out of the cap 28 to divert fluid away from the device 10. The external tube 32 replaces the internal tube that fits into the body of the device 10 as shown, for example, in FIGS. 1-7. As illustrated in FIG. 27C, fluid flows into the device 10 via the outer collection layer 40, is collected in the cap 28, and is subsequently diverted from the device 10 via the external tube 32 connected to the cap 28. The external tube 32 has numerous degrees of freedom, allowing the tube 32 to be positioned away from the patient as needed. In some embodiments, a hook 100 is provided on a top surface of the device 10 into which the external tube 32 is tucked or slid (e.g., to ensure that the external tube 32 is not accidentally pulled out of the cap 28 and the device 10). Alternatively, in some embodiments, the tube 32 is provided in the impermeable layer of the external covering 20 (e.g., in addition to, or instead of, a shape retaining element 90 provided in the impermeable layer of the external covering 20 similar to the element 90 shown in FIGS. 26A-B).

Further, the second end 34 of the external tube 32 is provided with a tubing adaptor 70 such that the tube 32 is connectable to a second length of tube (e.g., suction tubing) leading away from the patient or to another device (e.g., a suction device). FIGS. 28A-B illustrate exemplary embodiments of the adaptor 70. FIG. 28A illustrates a male adaptor 70, and FIG. 28B illustrates a female adaptor 70. The male adaptor 70 includes step tapering, for example, to help ensure that the adaptor 70 fits snugly within the second tube or device. By contrast, the female adaptor 70 includes an opening into which the second length of tube may be inserted and may also include step tapering within the opening. However, the adaptors 70 shown in FIGS. 28A-B are meant to be exemplary. As such, in other embodiments, the adaptor 70 is replaced with a different connector, such as a first side of a snap that fits into a corresponding second side of a snap on a suction tube/device, or a detent piece that fits inside of a suction tube/device. Additionally, in some embodiments, the adaptor includes or is connected to, or the external tube 32 is otherwise provided with, a diverter valve that allows a user to change the flow of fluid to a different attachment and/or a stop valve that allows a user to turn off the flow of fluid from the device 10. The diverter valve would allow for the flow of urine to a separate collection receptacle such as that meant for testing samples of the collected urine.

Figure 29A:
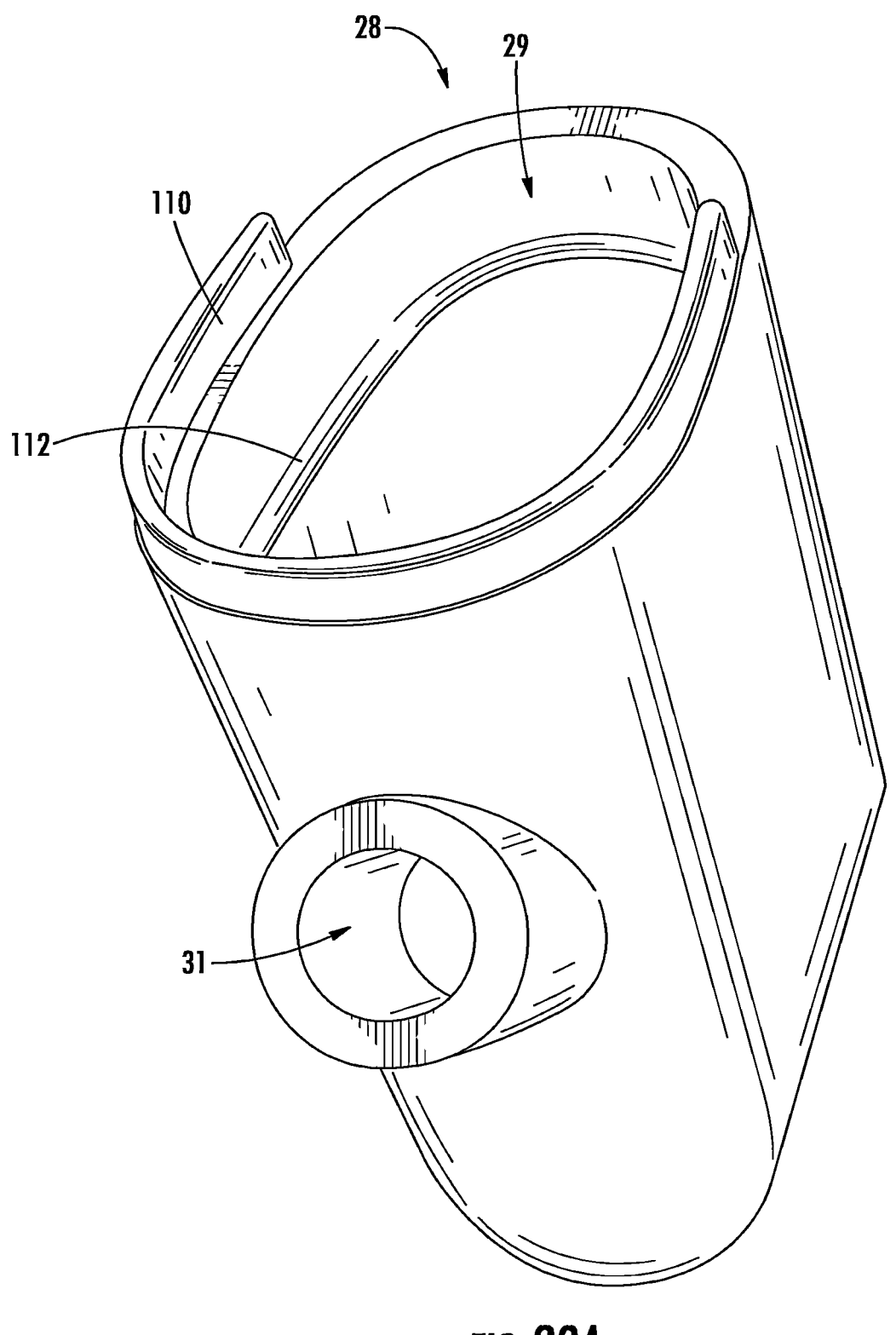
FIGS. 29A-B depict various perspective views of a cap of the device illustrated in FIGS. 27A-B, according to an exemplary embodiment.
Figure 29B:
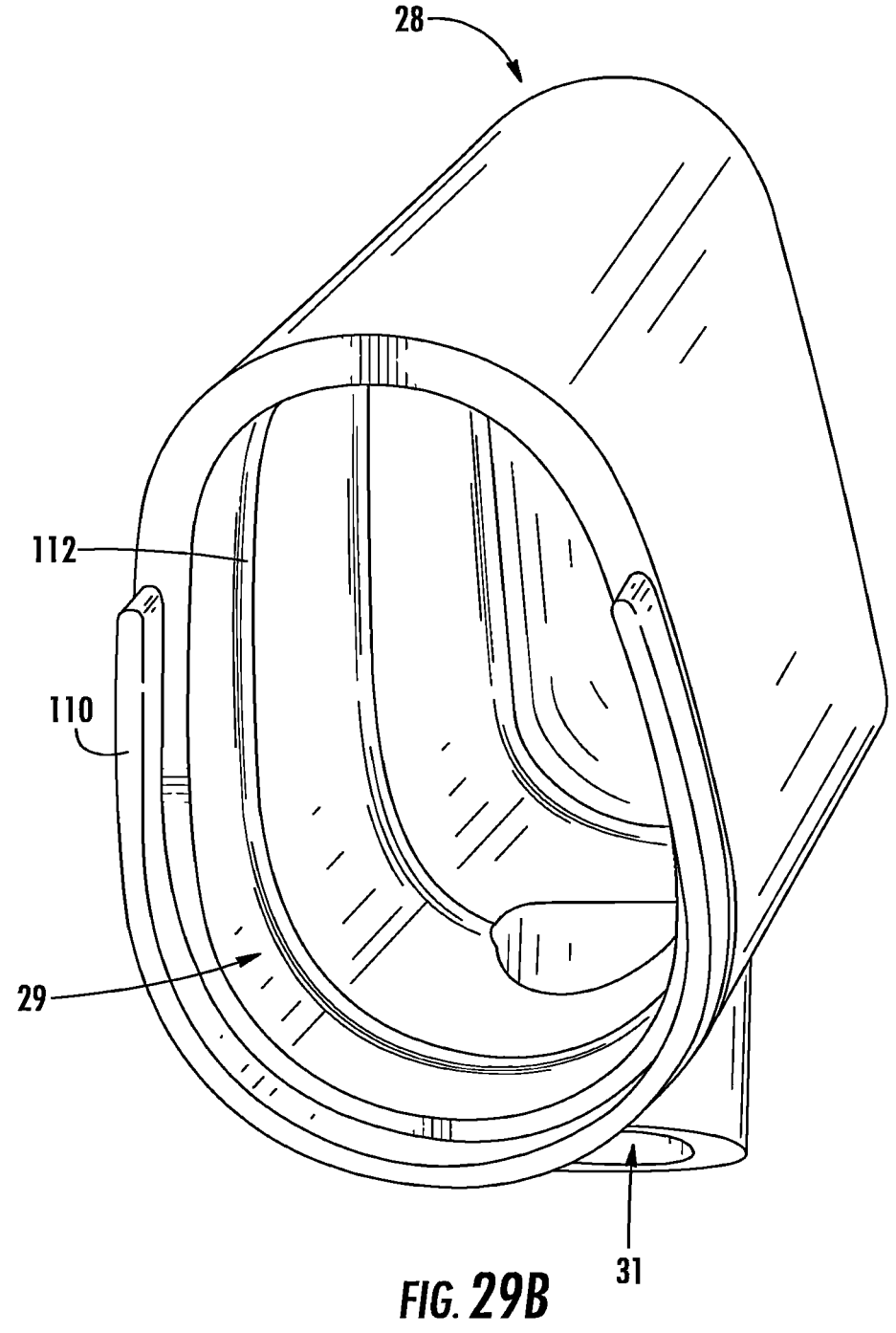

As discussed above, the first end 33 of the external tube 32 is inserted into the cap 28 to couple the tube 32 to the device 10. FIGS. 29A-B illustrate the cap 28, according to an exemplary embodiment. As shown in FIGS. 29A-B, the cap 28 has a smooth, elongated, wedge shape with curved sides configured to fit patient anatomy. The cap 28 includes an open end 29 configured to fit onto the open second end 24 of the device 10. The open end 29 includes a flange 110, and the inside surface of the cap 28 is provided with ribbing 112 to help ensure a snug fit between the cap 28 and the second end 24 of the device 10. The cap 28 also includes a port 31 into which the first end 33 of the external tube 32 is inserted to couple the tube 32 to the cap 28, for example, by threading the first end 33 into the port 31. As shown in FIGS. 27A-C, the port 31 extends near the open end 29 at an angle from the side of the cap 28. However, it should be understood that in other embodiments, the port 31 is provided anywhere on the cap 28 or, in some embodiments, elsewhere on the device 10. Alternatively, the cap 28 does not include a port 31 and may instead include a tubing adaptor 70 that connects directly to external suction tubing or an external suction device. In some embodiments, the cap 28 includes elements in addition to those depicted in FIGS. 29A-B, such as a relief valve or a holding element similar to the holding element described below with reference to FIGS. 30A-B.

Figure 30B:
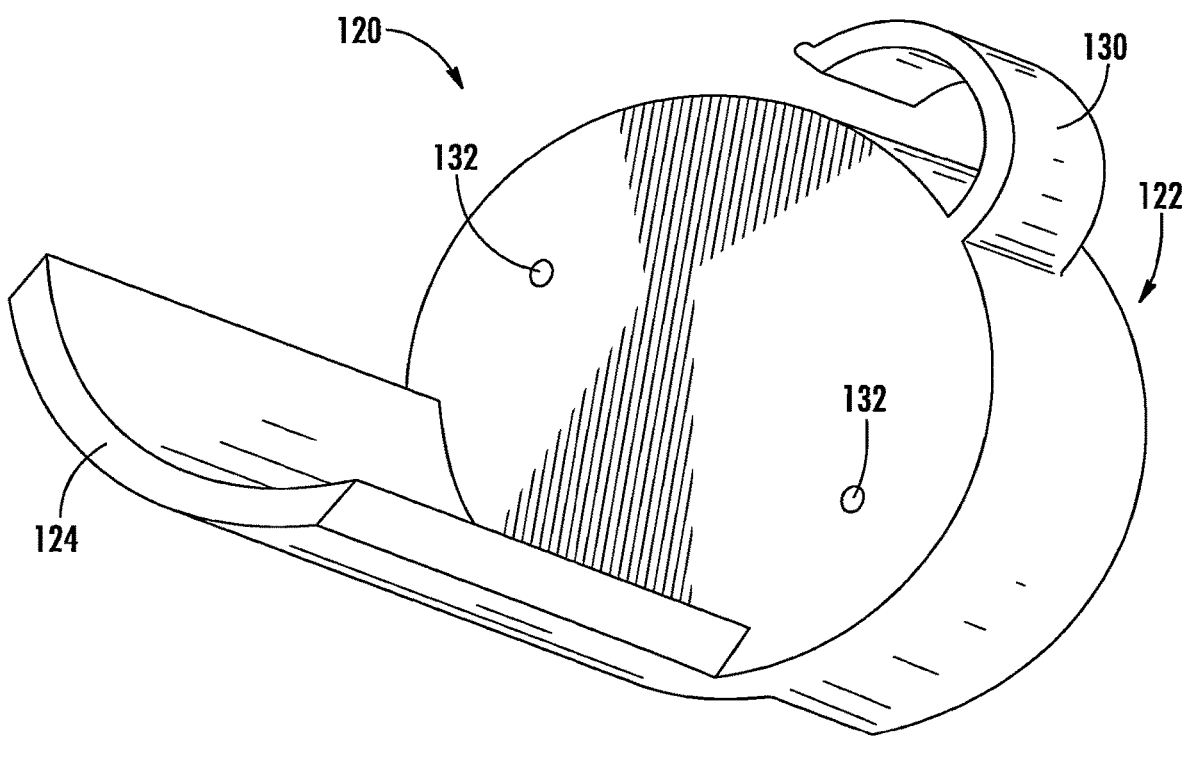

In some embodiments, the first end 33 of the device 10 is also provided with a cap, such as the top cap 120 illustrated in FIGS. 30A-B. As shown, the top cap 120 includes a connecting end 122 that extends out to form a tab 124, which is configured to secure the device 10 to the patient (e.g., by conforming to the patient's anatomy). The connecting end 122 includes a rim 126 configured to fit around the first end 22 of the device 10, as well as a holding feature 128 configured to hold an inside solid or tubular flexible element, such as a shape retaining element, through an annular fit. The connecting end 122 is also provided with a hook 130, which may be similar to the hook 100 and hold an external tube 32 in place during use of the device 10. The connecting end 122 also includes holes 132 that extend through the width of the connecting end 122 and serve as vent holes or valves to prevent skin suction (e.g., when the device 10 is connected to a suction element in order to vacate the device 10 of fluid).

Figure 31:
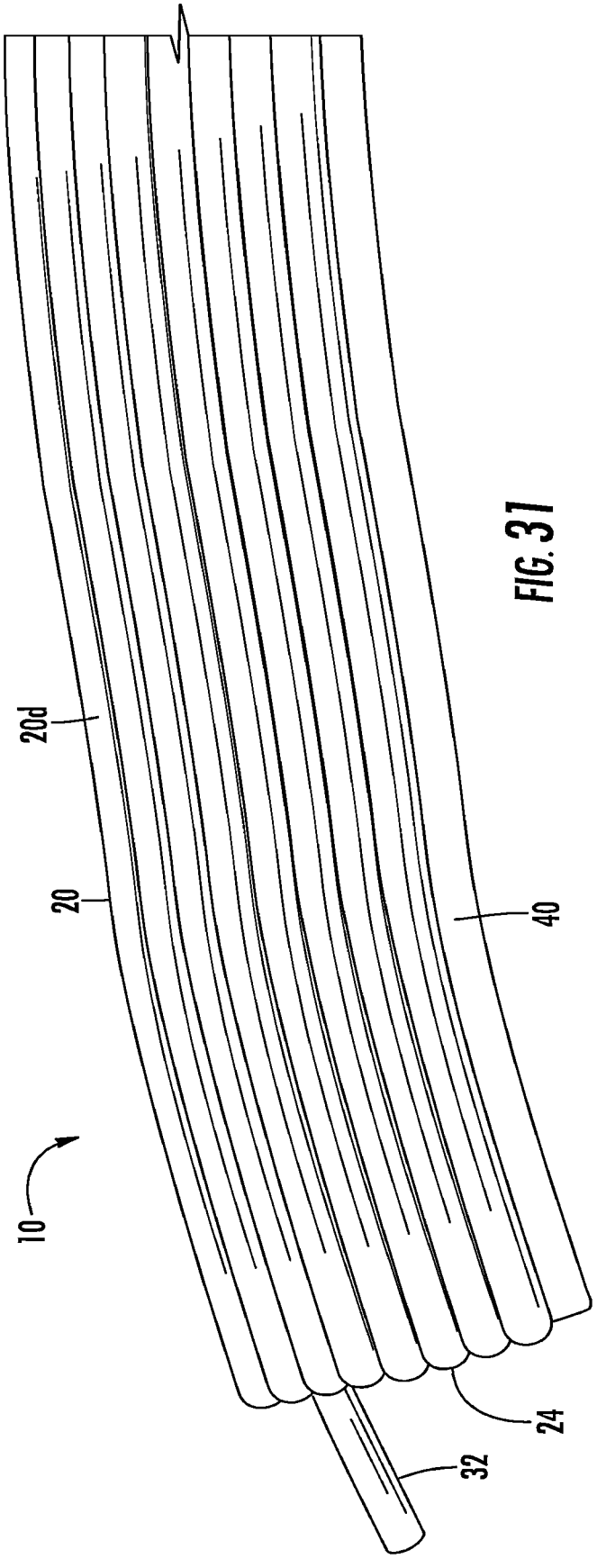
FIG. 31 depicts another embodiment of a urine collection device.

FIG. 31 illustrates another embodiment of a urine collection device 10 with the external covering 20 designed as a fluid impermeable backing. In the embodiment of FIG. 31, the external covering 20 is formed from a number of backing tubes 20d provided side-by-side to form a fluid impermeable surface. The backing tubes 20d are, for example, extruded together, adhered together, stitched together, or otherwise connected together to form the fluid impermeable surface of the external covering 20. Additionally, at least one of the backing tubes 20d is provided with the a tube 32 fitted within the backing tube 20d to allow for the direction of fluid into the cap 28 (not shown in FIG. 30) and out of the device 10.

The device 10 may be made of various materials and components as described above. Any of the materials used for the components of device 10 described above may be an antimicrobial material or fabric, or have an antimicrobial treatment applied thereto.

Referring now to FIG. 32, a system 200 for collecting urine that is discharged from the body of a user and carrying the collected urine away from the body is shown. The system includes the urine collection device 10 for collecting urine that is discharged from the body of a user. The system further includes discharge tube line 202 coupled to the tube 32 of the collection device 10 and disposed between the tube 32 and external collection reservoir 204. The system further includes an air pump or vacuum source 210 for providing suction through the tube 32, connected to the external receptacle via a vacuum line 212. In some embodiments, the discharge tube line 102 and the vacuum line 212 both comprise a flexible tubing (e.g., flexible plastic tubing). In some embodiments, the external reservoir 204 is a sealed container. In some embodiments, the external reservoir 204 is disposable. In some embodiments, the external collection reservoir 204 is configured to be sterilized after a use and reused. In some embodiments, tube 32 of the collection device 10 and the discharge tube line 202 are manufactured as a single piece of tubing.

The vacuum source 210 has a sufficiently high vacuum strength such that rapid air and liquid aspiration is maintained over at least a portion of the permeable membrane. In some embodiments, the vacuum source 210 can be a pump that is commercially available and configured to run continuously or sporadically. In some embodiments, the vacuum source 210 is a wall vacuum already integrated into the room of a medical facility. For example, the vacuum line 212 is directly connected to a vacuum regulator in the room.

Figure 33:
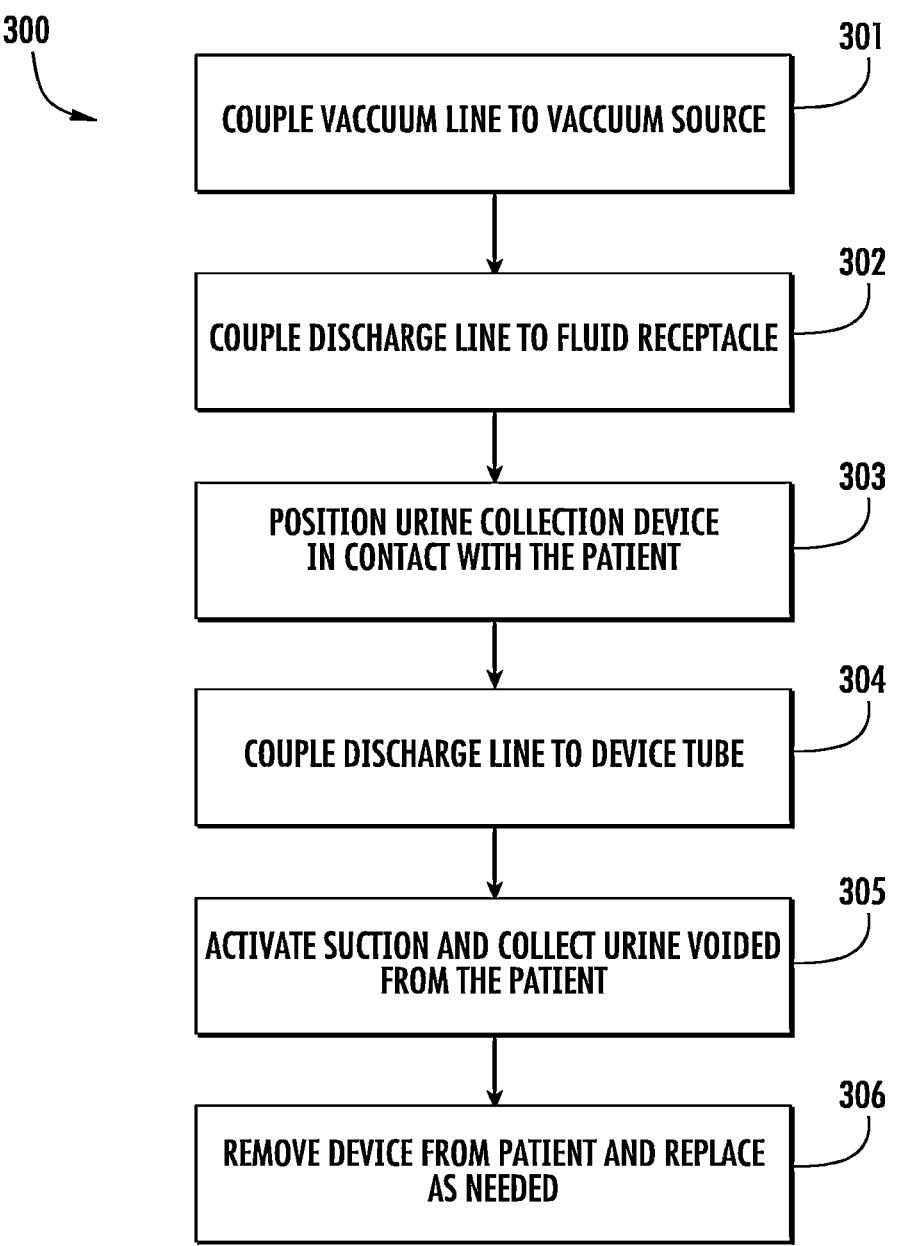
FIG. 33 is a flow chart depicting a method of using a urine collection device, according to an exemplary embodiment.

FIG. 33 is a flowchart illustrating an exemplary method 300 for using a device for collecting and evacuating urine that is discharged from the body of a patient. The device used in method 300 is the same or similar in structure and/or function to any of the devices disclosed and described with reference to FIGS. 1-31.

In step 301, the vacuum line 212 is coupled to the vacuum source 210. In step 302, the discharge tube line 202 is coupled to the fluid collection reservoir 204. In step 303, the urine collection device, such as urine collection device 10 is coupled to the patient. FIG. 34 is a flowchart depicting the substeps involved in step 303 for positioning the device on the patient.

In step 304, the free end of the discharge tube line 202 is coupled to the device 10, via the first end 33 of the tube 32. At this time, it should be confirmed that all tubing is free of obstacles. In some embodiments, the discharge tube line 202 is coupled to a curved tube extension 35. In step 305, suction is activated by way of the vacuum source such that urine voided from the patient can be collected and removed from the patient. In some embodiments, there could be continuous suction. In some uses, the suction remains activated for an extended period of time such that it is always effective for collecting and removing voided urine. In other uses, the suction is selectively activated only when needed, such as when the patient has voided.

In step 306, the device is removed from the body of a patient. Following step 306, the method may be repeated using a second, clean device for collecting and removing urine from the body of a patient. The device may need to be replaced periodically, such as every 12 or 24 hours, and should be disposed of according to hospital protocol. The anchor 50, if it is a separate piece, may be replaced after a longer period of time, such as 8, 12, 24, or 36 hours or longer. In some situations, the device may need to be replaced more or less often depending on several factors, including maintenance of proper positioning, leakage, volume of urine collected, and any other factors which may require sooner replacement or may allow the device to be used for a greater length of time.

At any time during the above method, a user or a caregiver may re-assess and correct the fit and positioning of the device, such as immediately after placement, after initial activation of the suction, after an extended period time, after patient repositioning, etc.

FIG. 34 is a flowchart depicted the sub-steps of positioning the device in contact with the patient in step 303. Prior to positioning the device, the caregiver may perform the proper hand hygiene and perineal care per hospital protocol. In step 401, the patient's legs are separated. In step 402, the patient's labia is separated using one hand. In step 403, using the other hand, the device is held vertically with cap 28 facing-downward and the fenestration 30 facing the patient's labia. Prior to this step, the caregiver may need to remove the device 10 from device packaging. In step 404, the edge of the device is aligned with the perineum and outer collection layer 40 is positioned against the urethral opening. In step 405, the cap 28 is secured between the patient's gluteal folds. In some embodiments where there is adhesive on the cap 28, the adhesive is secured between the patient's gluteal folds. In step 406, the labia is released.

In step 407, the anchor 50 is bent toward the pubic region. In this step, the caregiver may need to hold the device in this curvature until the anchor 50 is secured, or in the embodiment with the adjustable tube, the device will maintain this curvature after it is adjusted. In some cases, the device 10 already has the proper curvature such that no bending or adjustment is necessary. In step 408, the liner covering the adhesive is removed and the anchor 50 is smoothed over the patient's suprapubic region. Once the device is positioned and the proper placement is confirmed, the patient's legs should be closed to further secure the device in place.

Accordingly, when properly placed, the device should be positioned such that the at least one fenestration 30 of the device is in operative relation with a urethral opening of the patient such that urine discharged from the urethral opening is received by the device (e.g., the fluid collection assembly of the device, as described above) at the at least one fenestration 30. For example, the device should be positioned in a vertical orientation such that the at least one fenestration 30 is in operative relation with a urethral opening of a female patient. The urine is then directed into the cap 28, as described above, and evacuated from the device via the tube (e.g., via an internal tube 32 running inside the length of the device from the cap 28 to the open second end 24 or by an external tube 32 coupled to the cap 28). It should further be understood that a process similar to step 303 may be used to position the device with respect to a male patient but instead of separating and placing the device with respect to the patient's labia, the device is positioned, for example, in a cup-shaped configuration with at least one fenestration in operative relation with a urethral opening of a male user.

As utilized herein, the terms "approximately," "about," "substantially," and similar terms are intended to have a broad meaning in harmony with the common and accepted usage by those of ordinary skill in the art to which the subject matter of the present disclosure pertains. It should be understood by those of skill in the art who review the present disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the present disclosure as recited in the appended claims.

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the position of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

It is to be understood that although the present disclosure has been described with regard to embodiments thereof, those skilled in the art will readily appreciate that many modifications are possible (e.g., variations in sizes, structures, shapes and proportions of the various elements, mounting arrangements, use of materials, orientations, etc.) without materially departing from the novel teachings and advantages of the subject matter described herein. For example, the order or sequence of any process or method steps may be varied or re-sequenced according to alternative embodiments. Other substitutions, modifications, changes, and omissions may also be made in the design, operating conditions, and arrangement of the various exemplary embodiments without departing from the scope of the present disclosure.

With respect to the use of substantially any plural and/or singular terms herein, it should be understood that the plural to the singular and/or the singular to the plural may be translated as is appropriate to the context and/or application. The various singular/plural permutations may be expressly set forth herein for the sake of clarity.

What is claimed is:

1. A device for collecting urine discharged from a body of a user, comprising:

a fluid impermeable backing extending between a first end and a second end;

an outer collection layer having an outer surface that is configured to face the user and an inner surface that faces the fluid impermeable backing, wherein the fluid impermeable backing and the outer collection layer define a cavity that is configured to receive the urine from the body of the user;

an inner collection core extending along the inner surface of the outer collection layer;

a tube having (i) a first end extending out a first end of the cavity and (ii) a second end in fluid communication with a second end of the cavity; and an anchor directly coupled to the tube adjacent to the first end of the fluid impermeable backing, wherein the anchor extends laterally from opposing sides of the fluid impermeable backing, wherein the anchor comprises an adhesive layer, wherein a longitudinal axis extends between the first end and the second end, wherein a lateral axis extends between a first lateral side of the device and a second lateral side of the device, wherein the anchor is configured to extend from the fluid impermeable backing in a plane defined by the longitudinal axis and the lateral axis such that the adhesive layer is configured to lie in the plane and face the user while the outer collection layer faces the user, wherein the outer collection layer is configured to receive the urine into the cavity, and the tube is configured to remove the urine that is received into the cavity when suction is applied to the tube.

2. The device of claim 1, wherein the anchor comprises a center portion, a first wing portion extending from a first lateral side of the center portion, and a second wing portion extending from a second lateral side of the center portion.

3. The device of claim 2, wherein the center portion has a width that is smaller than a width of the first wing portion and a width of the second wing portion, and wherein the center portion has a length that is smaller than a length of the first wing portion and a length of the second wing portion.

4. The device of claim 2, wherein a portion of the anchor omits the adhesive layer.

5. The device of claim 4, wherein the anchor comprises the adhesive layer at an inner area and omits the adhesive layer at outer edges of the anchor.

6. The device of claim 2, wherein the anchor is configured to be coupled to a suprapubic region of the body of the user to position the outer collection layer facing a urethral opening of the body of the user.

7. The device of claim 2, wherein the center portion, the first wing portion, and the second wing portion are a unitary, monolithic structure.

8. The device of claim 1, wherein the anchor comprises an external film covering the adhesive layer, wherein the external film comprises one or more tabs that are configured to be gripped to remove the external film from the adhesive layer.

9. The device of claim 1, wherein the anchor overlaps a portion of the tube.

10. The device of claim 1, further comprising a curved tube extension coupled to the first end of the tube.

11. The device of claim 1, further comprising a means for biasing the device to a curved shape.

12. The device of claim 11, wherein the means for biasing the device to the curved shape comprises a spring biasing member that is configured to bias the device to the curved shape.

13. The device of claim 11, wherein the means for biasing the device to the curved shape comprises one or more memory shaped supports that are configured to bias the device to the curved shape.

14. The device of claim 13, wherein the one or more memory shaped supports are encased by the fluid impermeable backing.

15. The device of claim 14, wherein the tube is positioned next to the one or more memory shaped supports.

16. The device of claim 1, wherein the fluid impermeable backing comprises a first portion that is configured to be positioned at a pubic region of the body of the user and a second portion that is configured to be positioned at a perineum of the body of the user while the first portion is positioned at the pubic region.

17. The device of claim 16, wherein the fluid impermeable backing further comprises a third portion that is configured to be positioned at a coccyx of the body of the user while the first portion is positioned at the pubic region and the second portion is positioned at the perineum.

18. The device of claim 16, wherein the second portion has a width that is less than a width of the first portion.

19. The device of claim 1, further comprising a cap at the second end of the fluid impermeable backing.

20. The device of claim 1, wherein the inner collection core is between the tube and the outer collection layer.

21. The device of claim 1, wherein the fluid impermeable backing is coupled to the outer collection layer to define a fenestration for receiving the urine into the cavity through the outer collection layer.

22. The device of claim 1, wherein, in a dimension of the lateral axis, the anchor is greater in size than the cavity.

23. The device of claim 1, wherein the anchor has (i) a width in a dimension of the lateral axis, (ii) a length in a dimension of the longitudinal axis, and (iii) a thickness in a dimension that is orthogonal to the lateral axis and the longitudinal axis, and wherein the width of the anchor is greater than the length
  of the anchor and the length of the anchor is greater
  than the thickness of the anchor.

<div align="center">*   *   *   *   *</div>